US009290563B2

(12) United States Patent
Arnell et al.

(10) Patent No.: US 9,290,563 B2
(45) Date of Patent: Mar. 22, 2016

(54) VARIANT IMMUNOGLOBULINS WITH IMPROVED MANUFACTURABILITY

(71) Applicant: Lonza Biologics PLC, Slough, Berkshire (GB)

(72) Inventors: Andreas Arnell, Newmarket (GB); Jose Jimenez, London (GB); Rebecca Michael, Cambridge (GB); Yvette Stallwood, Newmarket (GB); Jesus Zurdo, Cambridge (GB)

(73) Assignee: Lonza Biologics PLC, Slough, Berkshire (GB)

( * ) Notice: Subject to any disclaimer, the term of this patent is extended or adjusted under 35 U.S.C. 154(b) by 0 days.

(21) Appl. No.: 14/589,066

(22) Filed: Jan. 5, 2015

(65) Prior Publication Data

US 2015/0104449 A1 Apr. 16, 2015

Related U.S. Application Data

(63) Continuation of application No. 13/390,996, filed as application No. PCT/GB2010/001579 on Aug. 20, 2010, now Pat. No. 8,951,516.

(60) Provisional application No. 61/241,717, filed on Sep. 11, 2009.

(30) Foreign Application Priority Data

Aug. 21, 2009 (GB) .................................. 0914691.1

(51) Int. Cl.
C07K 16/00 (2006.01)
A61K 39/395 (2006.01)

(52) U.S. Cl.
CPC ........... *C07K 16/00* (2013.01); *A61K 39/39591* (2013.01); *C07K 2317/522* (2013.01); *C07K 2317/565* (2013.01); *C07K 2317/567* (2013.01)

(58) Field of Classification Search
CPC .................. A61K 39/39591; C07K 2317/567; C07K 2317/565; C07K 2317/522
USPC ..................... 424/133.1; 435/69.6; 530/387.3
See application file for complete search history.

(56) References Cited

U.S. PATENT DOCUMENTS 7,582,733 B2 * 9/2009 Basi .................... A61K 38/1709
530/387.1
7,700,751 B2 * 4/2010 Basi ....................... C07K 16/18
530/387.1
2005/0244403 A1 11/2005 Lazar et al.

FOREIGN PATENT DOCUMENTS

| WO | 2003/074679 | 9/2003 |
| WO | 2005/045442 | 5/2005 |
| WO | 2009/155513 | 12/2009 |
| WO | 2011/021009 | 2/2011 |

OTHER PUBLICATIONS

Obrezanova et al. (Mabs 7(2):352-63 (2015); abstract only).*
Brorson et al., "Mutational analysis of avidity and fine specificity of anti-levan antibodies," J. Immunol., 163:6694-6701 (1999).
Brummell et al., "Probing the combining site of an anti-carbohydrate antibody by saturation-mutagenesis: role of the heavy-chain CDR3 residues," Biochemistry, 32:1180-1187 (1993).
Burks et al., "In vitro scanning saturation mutagenesis of an antibody binding pocket," PNAS, 94:412-417 (1997).
Chennamsetty et al., "Aggregation-Prone Motifs in Human Immunoglobulin G," J. Mol. Biol. 391(2): 404-413 (2009).
Chennamsetty et al., "Design of therapeutic proteins with enhanced stability," PNAS 106 (29): 11937-11942 (2009).
Coleman, "Effects of amino acid sequence changes on antibody-antigen interactions," Research in Immunol., 145:33-36 (1994).
Communication issued in EP10749484.1 on Oct. 20, 2014 (5 pages).
International Search Report and Written Opinion mailed Dec. 2, 2010 from international application No. PCT/BGB2010/001579, 19 pgs.
Jang et al., "The structural basis for DNA binding by an anti-DNA autoantibody," Molec. Immunol., 35:1207-1217 (1998).
Kipriyanov et al., "Two amino acid mutations in an anti-human CD3 single-chain Fv antibody fragment that affect the yield on bacterial secretion but not the affinity," Protein Engineering 4(1): 445-453 (1997).
Kobayashi et al., "Tryptophan H33 plays an important role in pyrimidine (6-4) pyrimidone photoproduct binding by a high-affinity antibody," Protein Engineering, 12:879-884 (1999).
Kugler et al., "Stabilization and humanization of a single-chain Fv antibody fragment specific for human lymphocyte antigen CD19 by designed point mutations and CDR-grafting onto a human framework," Protein Engineering 22(3): 135-147 (2009).
McDonagh et al., "Improved yield and stability of L49-sFv-beta-lactamase, a single-chain antibody fusion protein for anticancer prodrug activation, by protein engineering," Bioconjugate Chem. 14: 860-869 (2003).
Monsellier et al., "Improving the Stability of an Antibody Variable Fragment by a Combination of Knowledge-based Approaches: Validation and Mechanisms," J. Mol. Biol. 362: 580-593 (2006).

(Continued)

*Primary Examiner* — Lynn Bristol
(74) *Attorney, Agent, or Firm* — Fish & Richardson P.C.

(57) ABSTRACT

This invention relates to the modification of the amino acid sequence of an immunoglobulin molecule at certain key positions within regions of the VH and VL FR and CDR3 domains and/or the CH1 domain which are prone to aggregation. Immunoglobulins modified as described may display improved manufacturability, for example, reduced aggregation propensity and/or increased production levels.

9 Claims, No Drawings

(56) References Cited

OTHER PUBLICATIONS

Rudikoff et al., "Single amino acid substitution altering antigen-binding specificity," Proc. Natl. Acad. Sci. USA, 79:1979-1983 (1982).

Winkler et al., "Changing the Antigen Binding Specificity by Single Point Mutations of an Anti-p24 (HIV-1) Antibody," The Journal of Immunology, 165:4505-4514 (2000).

* cited by examiner

VARIANT IMMUNOGLOBULINS WITH IMPROVED MANUFACTURABILITY

CLAIM OF PRIORITY

This application is a continuation of U.S. patent application Ser. No. 13/390,996, filed on Feb. 17, 2012, which is a 371 of International Application No. PCT/GB2010/001579, filed Aug. 20, 2010, and claims the benefit of Great Britain Patent Application Serial No. 0914691.1, filed on Aug. 21, 2009, and U.S. Provisional Patent Application Ser. No. 61/241,717, filed Sep. 11, 2009, the entire contents of which are hereby incorporated by reference.

This invention relates to the expression of antibody molecules and, in particular, to the production of antibody molecules with improved manufacturability.

The term "aggregation" describes a broad variety of phenomena, all related to protein self-association, which can occur in multiple environments, from cell culture and fermentation, to isolation, purification and formulation processes. For example, 'aggregation' is often used when describing the formation of inclusions; the accumulation of protein in 'insoluble' fractions following cell fractionation; the appearance of turbidity, protein precipitation or formation of particles in samples; or the formation of small soluble oligomers amongst others. In this context, protein aggregation, understood as 'abnormal self-association' of polypeptide chains, can have multiple origins and manifestations which are largely dependent on both the nature of molecules involved and the environment in which polypeptides are produced, isolated, stored and administered.

The three-dimensional structure of a polypeptide determines its natural physiological function. Proteins typically acquire their native structure after being synthesised in the ribosome. The process of protein folding is fundamentally encoded in the amino acid sequence of a protein. However, folding can also be assisted in vivo by a number of molecular helpers and quality control mechanisms that ensure that polypeptides attain their intended biologically active structure, avoiding the population of aberrant conformations in the process. Such external helpers and quality control elements include chaperones, disulfide isomerases, post-translational modifications (i.e. proteolytic processing, acylation, glycosylation, etc.), and the ubiquitin-proteasome system.

Additionally, protein aggregation is driven by the intrinsic stability of proteins in solution. Proteins are only marginally stable in solution, and this relative low stability is crucial in conferring specific biological properties while offering good regulation mechanisms to control their action. However, taking polypeptides outside their natural environment, for example to develop them as drugs, imposes a number of strict restrictions in their production, isolation and formulation that can have a big impact on their stability and aggregation behaviour.

Alterations to the native environment of a given protein, particularly due to specific production or process requirements, can have dramatic impact on its yield and stability in solution. This problem is exacerbated by process requirements to increase yields, for example: artificial synthesis, heterologous expression (i.e. prokaryotic expression of mammalian proteins), the use of secretory versus non-secretory pathways, saturation of protein synthesis machinery; or additional hurdles posed by non-natural proteins, such as polypeptide fragments or fusions. For instance, the expression of mammalian proteins in heterologous systems poses numerous risks. This is due to the fact that such systems usually lack the adequate molecular environment to guarantee a 'native' folding and processing.

The present invention relates to the finding that modifying the amino acid sequence of immunoglobulin molecules in certain key positions leads to improvements in manufacturability, and in particular to reductions in aggregation propensity and/or increases in production levels.

An aspect of the invention provides a method of producing a variant immunoglobulin, comprising;
  providing a parent immunoglobulin,
    introducing a substitution into an aggregation-prone segment of a VL domain framework region and/or VL CDR3 of the parent immunoglobulin; and/or,
    introducing a substitution into an aggregation-prone segment of a VH framework region and/or a VH CDR3; and/or,
    introducing a substitution into an aggregation-prone segment of the CH1 constant region domain of the heavy chain (CH) of the parent immunoglobulin,
  thereby producing a variant immunoglobulin.

The variant immunoglobulin may have improved manufacturability relative to the parent immunoglobulin. For example, the variant immunoglobulin may display reduced aggregation-propensity, and/or increased productivity upon expression, relative to the parent immunoglobulin.

For example, a variant immunoglobulin may display an increase in productivity of at least 10%, at least 20%, at least 30%, at least 40%, at least 50%, at least 100%, at least 200%, or at least 500% relative to the parent immunoglobulin and/or a decrease in aggregation (i.e. a reduction in the proportion of molecules in the native state ensemble which are aggregated) of at least 10%, at least 20%, at least 30%, at least 40%, at least 50%, at least 80%, at least 90% or at least 99% relative to the parent immunoglobulin. A variant immunoglobulin may display a decrease in aggregation of up to 100% relative to the parent immunoglobulin (i.e. complete abolition of aggregation).

Improvements in manufacturability may result fully or partially from reduced aggregation-propensity relative to the parent immunoglobulin.

Aggregation-propensity relates to the tendency of the immunoglobulin to form insoluble aggregates after expression in a recombinant system. Reductions in aggregation propensity reduce the proportion of molecules in the native state ensemble of the immunoglobulin which exist in an aggregated form (Carpenter et al, 2009 J Pharm Sci. April; 98(4):1201-5). In other words, the proportion of molecules within the native state ensemble of a variant immunoglobulin which exist in an aggregated or insoluble form is lower than the proportion within the native state ensemble of the parent immunoglobulin.

A variant immunoglobulin may show less self-association or aggregation compared to a parent immunoglobulin either under native conditions or at increased temperature (e.g. 60° C.) (i.e. conditions under which the antigen binding site of an immunoglobulin does not unfold). Preferably, the variant immunoglobulin shows less self-association or aggregation than parent immunoglobulin under native conditions (e.g. conditions which do not lead to unfolding of the immunoglobulin).

Aggregation propensity as described herein is distinct from thermal refolding efficiency (TRE), which relates to the ability of a protein to correctly refold after thermal denaturation, and is typically measured using circular dichroism (CD) (Tanha et al Protein Eng Des Sel. 2006 November; 19(11): 503-9). Reductions in the aggregation propensity of an immunoglobulin as described herein may have little or no effect on the thermal refolding efficiency of the immunoglobulin. Thermal refolding efficiency is therefore independent of aggregation propensity and does not have a significant impact on the manufacturability of an immunoglobulin.

Aggregation may be measured by conventional methods. Suitable techniques include GP-HPLC, HPLC and AUC (Gabrielson J P et al J Pharm Sci 2007 96(2): 268-79), protein loss after filtration; turbidity; fluorescent dye binding (e.g. Nile Red, thioflavin T or 8-anilino-1-napthalenesulfonic acid; see for example Hawe, A. et al Pharmaceutical Research 2008 25 (7) 1487-99 or Demeule, B et al 2007 Int J Pharm 329: 37-45), field-flow fractionation (FFF; Demeule, B et al. mAbs 2009 1(2): 142-150), and analytical ultracentrifugation (AU/AUC; Liu J et cal. AAPS J 2006 8: 580-9).

Other suitable methods are described in Arvinte T. In "Methods for structural analysis of protein pharmaceuticals" AAPS Press, 2005: 661-6 and Kiese S et al J Pharm Sci 2008 97(10): 4347-66.

Improvements in manufacturability may result fully or partially from increased productivity relative to the parent immunoglobulin.

A variant immunoglobulin may display increased productivity than the parent immunoglobulin. For example, the variant immunoglobulin may show increased yields or titres compared to a parent immunoglobulin when expressed in a recombinant system, e.g. bacterial or mammalian cells. Productivity may be measured using standard techniques, such as the Bradford assay, spectrophotometry and ELISA.

A variant immunoglobulin may also display one or more of improved purification yields; reduced formulation problems; reduced immunogenicity and increased bioavailability relative to the parent immunoglobulin.

In preferred embodiments, improvements in manufacturability may result may result from both reduced aggregation-propensity and increased productivity relative to the parent immunoglobulin.

Preferably, a variant immunoglobulin displays the same or substantially the same activity as the parent immunoglobulin (i.e. antigen binding activity).

An immunoglobulin is a polypeptide or protein which comprises an antigen-binding site. An antigen-binding site is the part of an immunoglobulin which specifically binds to and is spatially complementary to part or all of an antigen. Where an antigen is large, an immunoglobulin may only bind to a particular part of the antigen, which part is termed an epitope. Preferably, an antigen binding domain comprises an immunoglobulin light chain variable region (VL) and an immunoglobulin heavy chain variable region (VH), which may be on the same or different polypeptide chains.

Examples of immunoglobulins include whole antibodies, including antibody isotypes, such as IgG, IgA, IgD, IgM and IgE and their isotypic subclasses, such as IgG1 and IgG4; antibody fragments; and engineered antibody derivatives, such as small immunoproteins (SIPs), minaturised antibodies, camelid VHH domains and diabodies.

Examples of antibody fragments include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH or VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al. Nature Biotech 14 1239-1245 1996). Minibodies comprising an scFv joined to a CH3 domain may also be made (S. Hu et al, Cancer Res. 56 3055-3061 1996).

Immunoglobulins may be natural or wholly or partially synthetic. Chimeric immunoglobulins may comprise an antigen binding domain, or equivalent, fused to another polypeptide are therefore included. Cloning and expression of chimeric antibodies are described in EP-A-0120694 and EP-A-0125023. Various artificial immunoglobulins including one or more antigen-binding sites have been engineered, including for example $Fab_2$, $Fab_3$, diabodies, triabodies, tetrabodies and minibodies.

In some preferred embodiments, parent and variant immunoglobulins as described herein are whole antibodies or antibody fragments comprising both VH and VL domains.

Immunoglobulins may be isolated or obtained by purification from natural sources, or else obtained by genetic recombination, or by chemical synthesis, as described herein. For example, synthetic immunoglobulins may be created by expression from genes generated by means of oligonucleotides synthesized and assembled within suitable expression vectors, as described by Knappik et al. J. Mol. Biol. (2000) 296, 57-86 or Krebs et al. Journal of Immunological Methods 254 2001 67-84.

Immunoglobulins may be glycosylated, either naturally, in vitro, or ex vivo, for example, using systems of heterologous eukaryotic cells (e.g. CHO cells), or they may be unglycosylated (for example if produced by expression in a prokaryotic cell). Preferably, a glycosylated immunoglobulin does not comprise fucose.

A suitable parent immunoglobulin may be any immunoglobulin which has a known amino acid sequence and is produced by recombinant expression in a heterologous expression system. Heterologous expression systems include mammalian cells, such as CHO cells, insect cells, yeast cells and bacterial cells, such as *E. coli*, in particular for antibody fragments, and are described in more detail below.

A suitable parent immunoglobulin for modification as described herein may display sub-optimal manufacturability. In other words, the parent immunoglobulin may display one or more undesirable production traits, such as increased aggregation and/or reduced productivity relative to control immunoglobulins, when expressed recombinantly at a manufacturing scale in a heterologous system.

Suitable control immunoglobulins include immunoglobulins of the same type which display satisfactory manufacturability in the same heterologous system. When expressed at a manufacturing scale in a mammalian system, a suitable parent immunoglobulin may, for example, produce yields of 1 g/L or less of soluble material, as measured by ELISA, and/or 5% or more aggregation, as measured by GP-HPLC. When expressed at a manufacturing scale in a bacterial system, a parent immunoglobulin may, for example, produce yields of 0.5 g/L or less of soluble material, as measured by ELISA, and/or 5% or more aggregation, as measured by GP-HPLC.

A method may comprise determining the manufacturability of a parent immunoglobulin, for example by measuring production levels and aggregation propensity as described herein. A parent immunoglobulin which produces low yields (e.g. 1 g/L or less of soluble material in a mammalian system)

and/or high aggregation propensity (e.g. 5% or more aggregation) may be identified as displaying sub-optimal manufacturability.

Modification of the sequence of the parent immunoglobulin as described herein may be useful in increasing or optimising its manufacturability.

In preferred embodiments, the parent immunoglobulin may be a therapeutic antibody i.e. an antibody which binds to a therapeutically relevant antigen to achieve a beneficial therapeutic effect. Numerous examples of therapeutic antibodies are known in the art.

A variant immunoglobulin is a non-naturally occurring immunoglobulin which binds to the same target antigen as the parent immunoglobulin but which possesses a different amino acid sequence. For example, the sequence of the variant immunoglobulin may differ in 1, 2, 3, 4, 5, 6, 7, 8, 9, 10 or more amino acid residues, relative to the sequence of the parent immunoglobulin. Preferably, the sequence of the variant immunoglobulin differs from the parent immunoglobulin sequence only by one or more substitutions in aggregation-prone segments, as described herein. In other words, with the exception of the one or more substitutions described herein, the sequence of the variant immunoglobulin is preferably identical to the amino acid sequence of the parent immunoglobulin.

The variant immunoglobulin binds to the same epitope as the parent immunoglobulin and competes for binding to the antigen with the parent immunoglobulin. Competition between immunoglobulins may be assayed easily in vitro, for example using ELISA and/or by tagging a specific reporter molecule to one immunoglobulin which can be detected in the presence of the other untagged immunoglobulin. When the parent immunoglobulin is a therapeutic antibody, the variant immunoglobulin preferably achieves the same beneficial therapeutic effect.

The antigen-binding domain of an immunoglobulin as described herein preferably comprises a heavy chain variable domain (VH) and a light chain variable domain (VL). Immunoglobulin VH and VL domains each comprise three CDRs (CDR1, CDR2 and CDR3) which are separated by framework regions (FR1, FR2, FR3 and FR4). CDRs are hypervariable regions within the variable domain which contain the majority of the amino acid residues responsible for the specific binding of the antibody for the antigen or the epitope which it recognizes. The length of the CDRs may vary from 2 to 26 amino acids, depending on the length that can be accommodated by the particular underlying framework.

Preferably, immunoglobulins for use as described herein lack intra- or inter-CDR disulphide linkages.

Suitable parent immunoglobulin CH1, VH and VL domains for use as described herein may be obtained from any germ line or rearranged human variable domain, or may be a synthetic variable domain based on consensus sequences of known human variable domains. In some embodiments, the VH and VL domains of a variant immunoglobulin which is produced may lack one or more CDR sequences (e.g. CDR3) for example for use in antibody engineering, as described below.

The variant immunoglobulin may display improved manufacturability such as reduced aggregation and/or increased productivity relative to the parent immunoglobulins when expressed recombinantly at a manufacturing scale in a heterologous system. When expressed at a manufacturing scale in a mammalian system, a variant immunoglobulin may, for example, produce yields of more than 1 g/L of soluble material, as measured by ELISA, and/or less than 5% aggregation, as measured by GP-HPLC. Preferably, a variant immunoglobulin as described herein both produces yields of more than 1 g/L of soluble material and displays less than 5% aggregation. When expressed at a manufacturing scale in a bacterial system, a variant immunoglobulin may, for example, produce yields of more than 0.5 g/L of soluble material, as measured by ELISA, and/or less than 5% aggregation, as measured by GP-HPLC. Preferably, the variant immunoglobulin as described herein both produces yields of more than 0.5 g/L of soluble material and displays less than 5% aggregation.

An aggregation-prone segment is a short sequence of amino acid residues within the light or heavy chain sequence of an immunoglobulin which has a high aggregation propensity relative to surrounding sequence and which adversely affects the manufacturability of the immunoglobulin. An aggregation-prone segment may consist of 1, 2, 3, 4, 5, 6, 7, 8, 9, or 10 amino acid residues An aggregation-prone segment may, for example, be located in the CH1, VH or VL domain of an immunoglobulin. A single domain or region of an immunoglobulin, such as a FR1, FR2, FR3, FR4 or CDR3 region from a VH or VL domain or a CH1 domain, may possess multiple aggregation-prone segments within its sequence. Substitution of one or more residues in one or more of these aggregation-prone segments as described herein may improve the manufacturability of the immunoglobulin as described herein.

The immunoglobulin residues position described below are numbered according to the scheme set out in Kabat, E. A., Wu, T. T., Perry, H. M., Gottesmann, K. S & Foeller, C. (1991). Sequences of Proteins of Immunological Interest, 5th edit., NIH Publication no. 91-3242. U.S. Department of Health and Human Services.

Where appropriate, the position of a substitution may be described relative to a Kabat numbered residue which is invariant in immunoglobulin sequences.

An alternative antibody numbering scheme is described in Honegger, A and Plückthun A. (2001). Yet Another Numbering Scheme for Immunoglobulin Variable Domains: An Automatic Modelling and Analysis Tool. *J. Mol. Biol* 309, 657-670. Tables 1a and 1b show the correspondence between the Honegger and Kabat numbering schemes An amino acid substituted into an aggregation-prone segment as described herein is preferably one of the 20 naturally occurring amino acids. Naturally occurring amino acids and their standard one and three letter abbreviations are well-known in the art (Principles of Protein Structure G. Schulz & R. Schirmer, (1979) Springer-Verlag NY Inc USA).

A substitution may be introduced into an aggregation-prone segment within a VL domain framework region of the parent immunoglobulin. A suitable aggregation-prone segment of a VL domain framework region may be selected from the group consisting of the position 20 aggregation-prone segment, the position 37 aggregation-prone segment, the position 45 aggregation-prone segment and the position 74 aggregation-prone segment.

The position 20 aggregation-prone segment is located in VL framework region 1 and extends from position 15 to position 23 of the VL domain.

A substitution within the position 20 aggregation-prone segment may occur at position 18 of the VL domain.

The amino acid residue at position 18 in the parent immunoglobulin may be replaced by a different amino acid residue in the variant immunoglobulin. Preferably, the residue at position 18 is substituted for R, S or V.

For example, the amino acid residue at position 18 in the parent immunoglobulin may be T. The variant immunoglobulin may comprise a VL domain which comprises a T18R, T18S or T18V substitution.

A substitution within the position 20 aggregation-prone segment may occur at position 20 of the VL domain.

The amino acid residue at position 20 in the parent immunoglobulin may be replaced by a different amino acid residue in the variant immunoglobulin. Preferably, the residue at position 20 is substituted for K, R, S or V.

For example, the amino acid residue at position 20 in the parent immunoglobulin may be T. The variant immunoglobulin may comprise a VL domain which comprises a T20K, T20R, T20S or T20V substitution.

The position 37 aggregation-prone segment is located in VL framework region 2 and extends from position 36 to position 38 of the VL domain.

A substitution within the position 37 aggregation-prone segment may occur at position 37.

The amino acid residue at position 37 in the parent immunoglobulin may be replaced by a different amino acid residue in the variant immunoglobulin. Preferably, the residue at position 37 is substituted for Q or N.

For example, the amino acid residue at position 37 in the parent immunoglobulin may be L. The variant immunoglobulin may comprise a VL domain which comprises a L37Q substitution.

The position 45 aggregation-prone segment is located in VL framework region 2 and extends from position 42 to position 49 of the VL domain.

A substitution within the position 45 aggregation-prone segment may occur at position 45.

The amino acid residue at position 45 in the parent immunoglobulin may be replaced by a different amino acid residue in the variant immunoglobulin. Preferably, the residue at position 45 is substituted for E, K, R, Q or V.

For example, the amino acid residue at position 45 in the parent immunoglobulin may be T. The variant immunoglobulin may comprise a VL domain which comprises a T45E, T45K, T45R, T45Q or T45V substitution. The amino acid residue at position 45 in the parent immunoglobulin may be Q. The variant immunoglobulin may comprise a VL domain which comprises a Q45E, Q45K or Q45R substitution.

A substitution within the position 45 aggregation-prone segment may occur at position 46.

The amino acid residue at position 46 in the parent immunoglobulin may be replaced by a different amino acid residue in the variant immunoglobulin. Preferably, the residue at position 46 is substituted for L, Y, K, R, H, F or S.

For example, the amino acid residue at position 46 in the parent immunoglobulin may be T. The variant immunoglobulin may comprise a VL domain which comprises a T46L or T46Y substitution. The amino acid residue at position 46 in the parent immunoglobulin may be L. The variant immunoglobulin may comprise a VL domain which comprises a L46K, L46R, L46H, L46F or L46S substitution.

The position 74 aggregation-prone segment is located in VL framework region 3 and extends from position 71 to position 77 of the VL domain sequence.

A substitution within the position 74 aggregation-prone segment may occur at position 74.

The amino acid residue at position 74 in the parent immunoglobulin may be replaced by a different amino acid residue in the variant immunoglobulin. Preferably, the residue at position 74 is substituted for V.

For example, the amino acid residue at position 74 in the parent immunoglobulin may be T. The variant immunoglobulin may comprise a VL domain which comprises a T74V substitution.

A substitution may be introduced into an aggregation-prone segment within a VL CDR3 of the parent immunoglobulin. A suitable aggregation-prone segment may be selected from the group consisting of the VL CDR3 N terminal aggregation-prone segment and the VL CDR3 C terminal aggregation-prone segment.

The VL CDR3 N terminal aggregation-prone segment extends from invariant residue C88 to the position eight amino acids C-terminal of residue C88 in the VL domain sequence. For example, the VL CDR3 N terminal aggregation-prone segment may extend from position 88 to position 95a of the VL domain.

The amino acid residue at one or more of positions 88 (C88), 89 (C88+1; i.e. one residue C-terminal of residue C88), 90 (C88+2), 91 (C88+3), 92 (C88+4), 93 (C88+5), 94 (C88+6), 95 (C88+7) and 95a (C88+8) in the parent immunoglobulin may be replaced by a different amino acid residue in the variant immunoglobulin. The VL CDR3 positions numbered relative to invariant Kabat residue C88 are shown in brackets.

A substitution within the VL CDR3 N terminal aggregation-prone segment may occur at position 91 (C88+3).

The amino acid residue at position 91 in the parent immunoglobulin may be replaced by a different amino acid residue in the variant immunoglobulin. Preferably, the residue at position 91 is substituted for A, F, L, R, S or W. For example, the amino acid residue at position 91 in the parent immunoglobulin may be Y. The variant immunoglobulin may comprise a VL domain which comprises a Y91A, Y91F, Y91L, Y91R, Y91S or Y91W substitution.

A substitution within the VL CDR3 N terminal aggregation-prone segment may occur at position 93 (C88+5).

The amino acid residue at position 93 in the parent immunoglobulin may be replaced by a different amino acid residue in the variant immunoglobulin. Preferably, the residue at position 93 is substituted for D, F, L, Q, S, T, W or Y. For example, the amino acid residue at position 93 in the parent immunoglobulin may be P and the variant immunoglobulin may comprise a VL domain which comprises a P93D, P93F, P93L, P93Q, P93S, P93T, P93W or P93Y substitution.

The VL CDR3 C terminal aggregation-prone segment extends from the position three amino acids N-terminal of invariant residue F98 (i.e. position F98−3 or 95) to position 99 in the VL domain sequence.

The amino acid residue at one or more of positions 95 (F98−3), 96 (F98−2), 97 (F98−1), 98 or 99 in the parent immunoglobulin may be replaced by a different amino acid residue in the variant immunoglobulin.

A substitution within the VL CDR3 C terminal aggregation-prone segment may occur at position 96 (F98−2). The VL CDR3 position as numbered by proximity to Kabat residue F98 is shown in brackets.

The amino acid residue at position 96 in the parent immunoglobulin may be replaced by a different amino acid residue in the variant immunoglobulin. Preferably, residue at position 96 is substituted for E, L, V or W.

For example, the amino acid residue at position 96 in the parent immunoglobulin may be R and the variant immunoglobulin may comprise a VL domain which comprises a R96E, R96L, R96V or R96W substitution.

A substitution may be introduced into an aggregation-prone segment within a VH domain framework region of the parent immunoglobulin. A suitable aggregation-prone segment of a VH domain framework region may be selected from the group consisting of the FR1 aggregation-prone segment; the position 75 aggregation-prone segment; the position 95 aggregation-prone segment; and the position 102 aggregation-prone segment (or CDR3 aggregation-prone segment).

The FR1 aggregation-prone segment is located in VH framework region 1 and may for example extend from position 1 to position 21 of the VH domain sequence.

A VH FR1 aggregation-prone segment may comprise an aggregation-prone segment selected from the group consisting of positions 1 to 3; positions 4 to 6, positions 11 to 13, and positions 16 to 21.

A VH FR1 aggregation-prone segment may extend from position 1 to position 3 of the VH domain sequence.

A substitution within the VH FR1 aggregation-prone segment may occur at position 1.

The amino acid residue at position 1 in the parent immunoglobulin may be replaced by a different amino acid residue in the variant immunoglobulin. Preferably, the residue at position 1 is substituted for E, Q, D, A or V. For example, the amino acid residue at position 1 in the parent immunoglobulin may be E and the variant immunoglobulin may comprise a VH domain which comprises a E1Q, E1D, E1A or E1V substitution or the amino acid residue at position 1 in the parent immunoglobulin may be Q and the variant immunoglobulin may comprise a VH domain which comprises an Q1E, Q1D, Q1A or Q1V substitution.

A VH FR1 aggregation-prone segment may extend from position 4 to position 6 of the VH domain.

A substitution within the VH FR1 aggregation-prone segment may occur at position 5 of the VH domain.

The amino acid residue at position 5 in the parent immunoglobulin may be replaced by a different amino acid residue in the variant immunoglobulin. Preferably, the residue at position 5 is substituted for V. For example, the amino acid residue at position 5 in the parent immunoglobulin may be L and the variant immunoglobulin may comprise a VH domain which comprises a L5V substitution.

A VH FR1 aggregation-prone segment may extend from position 11 to position 13 of the VH domain.

A substitution within the VH FR1 aggregation-prone segment may occur at position 12 of the VH domain.

The amino acid residue at position 12 in the parent immunoglobulin may be replaced by a different amino acid residue in the variant immunoglobulin. Preferably, the residue at position 12 is substituted for V. For example, the amino acid residue at position 12 in the parent immunoglobulin may be L and the variant immunoglobulin may comprise a VH domain which comprises a L12V substitution.

A VH FR1 aggregation-prone segment may extend from position 16 to position 21 of the VH domain.

A substitution within the VH FR1 aggregation-prone segment may occur at position 17.

The amino acid residue at position 17 in the parent immunoglobulin may be replaced by a different amino acid residue in the variant immunoglobulin. Preferably, the residue at position 17 is substituted for R. For example, the amino acid residue at position 17 in the parent immunoglobulin may be G and the variant immunoglobulin may comprise a VH domain which comprises a G17R substitution.

A substitution within the VH FR1 aggregation-prone segment may occur at position 19.

The amino acid residue at position 19 in the parent immunoglobulin may be replaced by a different amino acid residue in the variant immunoglobulin. Preferably, the residue at position 19 is substituted for T or V. For example, the amino acid residue at position 19 in the parent immunoglobulin may be L and the variant immunoglobulin may comprise a VH domain which comprises a L19T or L19V substitution.

A substitution within the VH FR1 aggregation-prone segment may occur at position 20.

The amino acid residue at position 20 in the parent immunoglobulin may be replaced by a different amino acid residue in the variant immunoglobulin. Preferably, the residue at position 20 is substituted for A, K, S or T. For example, the amino acid residue at position 20 in the parent immunoglobulin may be R and the variant immunoglobulin may comprise a VH domain which comprises a R20A, R20K, R20S or R20T substitution.

A position 75 aggregation-prone segment may extend from position 60 to position 85 of the VH domain.

A substitution within the position 75 aggregation-prone segment may occur at position 61.

The amino acid residue at position 61 in the parent immunoglobulin may be replaced by a different amino acid residue in the variant immunoglobulin. For example, the residue at position 61 may substituted for K R Q E D N or A. Preferably, the residue at position 61 is substituted for R. For example, the amino acid residue at position 61 in the parent immunoglobulin may be P and the variant immunoglobulin may comprise a VH domain which comprises a P61R substitution.

A substitution within the position 75 aggregation-prone segment may occur at position 85.

The amino acid residue at position 85 in the parent immunoglobulin may be replaced by a different amino acid residue in the variant immunoglobulin. For example, the residue at position 85 may substituted for E, D or A. Preferably, the residue at position 85 is substituted for E. For example, the amino acid residue at position 85 in the parent immunoglobulin may be V and the variant immunoglobulin may comprise a VH domain which comprises a V85E, V85D or V85A substitution.

The VH position 95 aggregation-prone segment is located in VH framework region 3 and may extend from position 91 to position 99 or 100.

The amino acid residue at one or more of positions 91, 92, 93, 94, 95, 96, 97, 98, 99 and/or 100 in the VH domain of the parent immunoglobulin may be replaced by a different amino acid residue in the variant immunoglobulin.

A substitution within the VH position 95 aggregation-prone segment may occur at position 94.

The amino acid residue at position 94 in the parent immunoglobulin may be replaced by a different amino acid residue in the variant immunoglobulin. For example, the residue at position 94 may substituted for R, K or T. Preferably, the residue at position 94 is substituted for R. For example, the amino acid residue at position 94 in the parent immunoglobulin may be K and the variant immunoglobulin may comprise a VH domain which comprises a K94R or the substitution the amino acid residue at position 94 in the parent immunoglobulin may be H and the variant immunoglobulin may comprise a VH domain which comprises a H94R, H94K or H94T substitution.

A substitution within the VH position 95 aggregation-prone segment may occur at position 95.

The amino acid residue at position 95 in the parent immunoglobulin may be replaced by a different amino acid residue in the variant immunoglobulin. For example, the residue at position 95 may substituted for E or D. Preferably, the residue at position 95 is substituted for D. For example, the amino acid residue at position 95 in the parent immunoglobulin may be R and the variant immunoglobulin may comprise a VH domain which comprises a R95E or an R95D substitution.

A substitution within the VH position 95 aggregation-prone segment may occur at position 96.

The amino acid residue at position 96 in the parent immunoglobulin may be replaced by a different amino acid residue in the variant immunoglobulin. Preferably, the residue at position 96 is substituted for A. For example, the amino acid residue at position 96 in the parent immunoglobulin may be G and the variant immunoglobulin may comprise a VH domain which comprises a G96A substitution.

A substitution within the VH position 95 aggregation-prone segment may occur at position 100.

The amino acid residue at position 100 in the parent immunoglobulin may be replaced by a different amino acid residue in the variant immunoglobulin. The residue at position 100 may be substituted for F, G, L, M, or P. Preferably, the residue at position 100 is substituted for F. For example, the amino acid residue at position 100 in the parent immunoglobulin may be V and the variant immunoglobulin may comprise a VH domain which comprises a V100F, V100G, V100L, V100M, or V100P substitution.

A substitution may be introduced into the VH CDR3 aggregation-prone segment of the parent immunoglobulin.

The VH CDR3 aggregation-prone segment extends from position 100c (i.e. two amino acids N-terminus of invariant residue D101 or D101−2 as numbered relative to Kabat residue D101) to position 102 or position 103.

The amino acid residue at one or more of positions D101−2, D101−1, (two or one amino acids N-terminal of residue D101), 101, 102 and 103 in the VH domain of the parent immunoglobulin may be replaced by a different amino acid residue in the variant immunoglobulin.

A substitution within the VH CDR3 aggregation-prone segment may occur at position D101−2 (two amino acids N-terminal of residue D101).

The amino acid residue at position D101−2 in the parent immunoglobulin may be replaced by a different amino acid residue in the variant immunoglobulin. Preferably, the residue at position D101−2 is substituted for D, E, F, G, P, S, T, W, or Y. For example, the amino acid residue at position D101−2 in the parent immunoglobulin may be A and the variant immunoglobulin may comprise a VH domain which comprises an A(D101−2)D, A(D101−2)E, A(D101−2)F, A(D101−2)G, A(D101−2)P, A(D101−2)S, A(D101−2)T, or A(D101−2)W, or A(D101−2)Y substitution. In other words a substitution from A to D, E, F, G, P, S, T, W, or Y at the position two amino acids N-terminus of D101, for example A100c.

A substitution within the VH CDR3 aggregation-prone segment may occur at position D101−1 (one amino acid N-terminal of D101).

The amino acid residue at position D101−1 in the parent immunoglobulin may be replaced by a different amino acid residue in the variant immunoglobulin. Preferably, the residue at position D101−1 is substituted for F, G, L, P or M. For example, the amino acid residue at position D101−1 in the parent immunoglobulin may be S and the variant immunoglobulin may comprise a VH domain which comprises an S(D101−1)F, S(D101−1)G, S(D101−1)L, S(D101−1)P or S(D101−1)M substitution. In some embodiments, residue S(D101−1) corresponds to S100d.

A substitution within the VH CDR3 aggregation-prone segment may occur at position 102.

The amino acid residue at position 102 in the parent immunoglobulin may be replaced by a different amino acid residue in the variant immunoglobulin. Preferably, the residue at position 102 is substituted for A, F, H, I, L, V or Y. For example, the amino acid residue at position 102 the parent immunoglobulin may be P and the variant immunoglobulin may comprise a VH domain which comprises an P102A, P102F, P102H, P102I, P102L, P102Y or P102V substitution or the amino acid residue at position 102 the parent immunoglobulin may be S and the variant immunoglobulin may comprise a VH domain which comprises an S102A, S102F, S102H, S102I, S102L, S102Y or S102V substitution.

A substitution within the VH CDR3 aggregation-prone segment may occur at position 103.

The amino acid residue at position 103 in the parent immunoglobulin may be replaced by a different amino acid residue in the variant immunoglobulin. Preferably, the residue at position 103 is substituted for I, L or V. For example, the amino acid residue at position 103 in the parent immunoglobulin may be W and the variant immunoglobulin may comprise a VH domain which comprises a W103I, W103L or W103V substitution.

The CH1 aggregation-prone segment extends from position 150 to position 156.

A substitution within the CH1 aggregation-prone segment may occur at position 153.

The amino acid residue at position 153 in the parent immunoglobulin may be replaced by a different amino acid residue in the variant immunoglobulin. Preferably, the residue at position 153 is substituted for V. For example, the amino acid residue at position 153 in the parent immunoglobulin may be S and the variant immunoglobulin may comprise a CH1 domain which comprises a S153V substitution.

A variant immunoglobulin may comprise up to 10 substitutions as described herein relative to the parent immunoglobulin sequence. For example, a variant immunoglobulin may comprise up to 1, 2, 3, 4, 5, 6, 7, 8, 9 or 10 substitutions.

The substitutions may be in the same aggregation-prone segment or in different aggregation prone segments. For example, the variant immunoglobulin may comprise substitutions in 1, 2, 3, 4 or more different aggregation-prone segments as described herein. A variant immunoglobulin may comprise substitutions in the VH domain, the VL domain and/or in the CH1 region.

Any combination of the substitutions described herein may be employed. Examples of suitable combinations of substitutions are shown in Table 3a and 3b.

In some embodiments, a variant immunoglobulin may comprise 2 substitutions in the VL FR1 and/or FR2 domain; 3 substitutions in the VL CDR3 domain; 2 substitutions in the VL FR2 domain and 3 substitutions in the VL CDR3 domain; 2 substitutions in the VL FR1 domain, 2 substitutions in the VL FR2 domain and 3 substitutions in the VL CDR3 domain; 2 substitutions in the VH FR1 domain; 1 substitution in the VH FR1 domain and 1 substitution in the VH CDR3 domain; 2 substitutions in the VH CDR3 domain; or 1 substitution in the CH1 domain and 1 substitution in the VH FR1 domain.

A variant immunoglobulin may comprise two substitutions in the position 20 aggregation prone segment. For example, a variant immunoglobulin may comprise a VL domain which comprises substitutions at both positions 18 and 20 as described above. For example, the residues at both positions 18 and 20 may be substituted for R. A VL domain may, for example, comprise T18R and T20R substitutions.

A variant immunoglobulin may comprise a substitution in the position 20 aggregation prone segment and a substitution in the position 74 aggregation prone segment. For example, a variant immunoglobulin may comprise a VL domain which comprises substitutions at both positions 18 and 74 as described above. For example, the residue at position 18 may be substituted for R and the residue at position 74 may be substituted for V. A VL domain may, for example, comprise T18R and T74V substitutions.

A variant immunoglobulin may comprise two substitutions in the position 45 aggregation prone segment. For example, a variant immunoglobulin may comprise a VL domain which comprises substitutions at both positions 45 and 46 as described above. For example, the residue at position 45 may be substituted for K or R and the residue at position 46 may be substituted for L. A VL domain may, for example, comprise T45K (or T45R) and T46L substitutions.

A variant immunoglobulin may comprise two substitutions in the position 20 aggregation prone segment and two substitutions in the position 45 aggregation prone segment. For example, a variant immunoglobulin may comprise a VL domain which comprises substitutions at positions 18, 20, 45 and 46 as described above. For example, the residues at both positions 18 and 20 may be substituted for R, the residue at position 45 may be substituted for K or R and the residue at position 46 may be substituted for L. A VL domain may, for example, comprise T18R, T20R, T45K, and T46L substitutions or T18R, T20R, T45R and T46L substitutions.

A variant immunoglobulin may comprise two substitutions in the VL CDR3 N terminal aggregation-prone segment. For example, a variant immunoglobulin may comprise a VL domain which comprises substitutions at positions 91 (C88+3), 93 (C88+5), and 96 (F98−2) as described above. For example, the residue at position 91 may be substituted for W, the residue at position 93 may be substituted for Q and the residue at position 96 may be substituted for V. A VL domain may, for example, comprise Y91W (C88+3), P93Q (C88+5), and R96V (F98−2) substitutions.

A variant immunoglobulin may comprise two substitutions in the position 45 aggregation prone segment and two substitutions in the VL CDR3 N terminal aggregation-prone segment. For example, a variant immunoglobulin may comprise a VL domain which comprises substitutions at positions 45, 46, 91 (C88+3), 93 (C88+5), and 96 (F98−2) as described above. For example, the residue at position 45 may be substituted for K or R, the residue at position 46 may be substituted for L, the residue at position 91 may be substituted for W, the residue at position 93 may be substituted for Q and the residue at position 96 may be substituted for V. A VL domain may, for example, comprise T45K, T46L, Y91W (C88+3), P93Q (C88+5), and R96V (F98−2) substitutions or T45R, T46L, Y91W (C88+3), P93Q (C88+5), and R96V (F98−2) substitutions.

A variant immunoglobulin may comprise two substitutions in the position 20 aggregation prone segment, two substitutions in the position 45 aggregation prone segment, and two or three substitutions in the VL CDR3 N terminal aggregation-prone segment. For example, a variant immunoglobulin may comprise a VL domain which comprises substitutions at positions 18, 20, 45, 46, 91 (C88+3), 93 (C88+5), and 96 (F98−2) as described above. For example, the residues at both positions 18 and 20 may be substituted for R, the residue at position 45 may be substituted for K or R, the residue at position 46 may be substituted for L, the residue at position 91 may be substituted for W, the residue at position 93 may be substituted for Q and the residue at position 96 may be substituted for V. A VL domain may, for example, comprise T18R, T20R, T45K, T46L, Y91W (C88+3), P93Q (C88+5), and R96V (F98−2) substitutions or T18R, T20R, T45R, T46L, Y91W (C88+3), P93Q (C88+5), and R96V (F98−2) substitutions.

A variant immunoglobulin may comprise a VL domain which comprises substitutions in the VL position 37 aggregation-prone segment and the VL position 45 aggregation-prone segment. For example, a variant immunoglobulin may comprise a VL domain which comprises substitutions at positions 37 and 45 as described above. For example, the residue at position 37 may be substituted for Q or N and the residue at position 45 may be substituted for E, K or R. A VL domain may, for example, comprise L37Q and Q45R substitutions.

A variant immunoglobulin may comprise a VH domain which comprises substitutions in the VH FR1 aggregation-prone segment and the VH CDR3 aggregation-prone segment.

For example, a variant immunoglobulin may comprise a VH domain which comprises substitutions at both positions 1 and 102 as described above. For example, the residue at position 1 may be substituted for Q, A, E or V and the residue at position 102 may be substituted for Y. A VH domain may, for example, comprise Q1A and P102Y substitutions, Q1E and P102Y substitutions, Q1V and P102Y substitutions, E1A and P102Y substitutions, E1Q and P102Y substitutions, or E1V and P102Y substitutions.

In other examples, a variant immunoglobulin may comprise a VH domain which comprises substitutions at both positions 1 and 103 as described above. For example, the residue at position 1 may be substituted for Q, A, D, E or V and the residue at position 103 may be substituted for L. A VH domain may, for example, comprise Q1A and W103L substitutions, Q1E and W103L substitutions, Q1D and W103L substitutions, Q1V and W103L substitutions, E1A and W103L substitutions, E1Q and W103L substitutions, E1D and W103L substitutions or E1V and W103L substitutions.

A variant immunoglobulin may comprise two substitutions in the VH CDR3 aggregation-prone segment.

For example, a variant immunoglobulin may comprise a VH domain which comprises substitutions at both positions 100c (D101−2) and 100d (D101−1) as described above. For example, the residue at position 100c may be substituted for W and the residue at position 100d may be substituted for F. A VH domain may, for example, comprise A100cW and S100dF substitutions.

In other examples, a variant immunoglobulin may comprise a VH domain which comprises substitutions at both positions 100d (D101−1) and 102 as described above. For example, the residue at position 100d may be substituted for F or M and the residue at position 102 may be substituted for V or Y. A VH domain may, for example, comprise S100dF and P102V substitutions, S100dM and P102V substitutions, S100dF and P102Y substitutions or S100dM and P102Y substitutions.

In other examples, a variant immunoglobulin may comprise a VH domain which comprises substitutions at both positions 102 and 103 as described above. For example, the residue at position 102 may be substituted for V or Y and the residue at position 103 may be substituted for L, I or V. A VH domain may, for example, comprise P102Y and W103L substitutions, P102Y and W103I substitutions, P102Y and W103V substitutions, P102V and W103L substitutions, P102V and W103I substitutions, or P102V and W103V substitutions.

A variant immunoglobulin may comprise a VH domain which comprises substitutions in the VH position 95 aggregation-prone segment and the VH CDR3 aggregation-prone segment. For example, a variant immunoglobulin may comprise a VH domain which comprises substitutions at both positions 95 and 102 as described above. For example, the residue at position 95 may be substituted for E or D, and the residue at position 102 may be substituted for A F H I L V or Y. A VH domain may, for example, comprise R95D and S102V substitutions. Optionally a VH domain may further comprise substitutions at both positions 94 and 100 as described above. For example, the residue at position 94 may be substituted for R, K or T, and the residue at position 100 may be substituted for F, G, L, M or P. A VH domain may, for example, comprise H94R, R95D, V100F and S102V substitutions.

A variant immunoglobulin may comprise substitutions in the CH1 aggregation-prone segment and the VH position 19 aggregation-prone segment. For example, a variant immunoglobulin may comprise a CH1 domain which comprises a substitution at position 153 and a VH domain which comprises a substitution at position 19 as described above. For example, the residue at position 153 may be substituted for V and the residue at position 19 may be substituted for T. An immunoglobulin may for example, comprise an S153V substitution in the CH1 domain and an L19T substitution in the VH domain.

In other examples, a variant immunoglobulin may comprise a CH1 domain which comprises a substitution at position 153 as described above and a VH domain which comprises a substitution at position 20 as described above. For example, the residue at position 153 may be substituted for V and the residue at position 20 may be substituted for A. A variant immunoglobulin may, for example, comprise S153V and R20A substitutions.

A variant immunoglobulin may comprise a VL domain which comprises a substitution in the VL position 20 aggregation-prone segment and a VH domain which comprises a substitution in the VH FR1 aggregation-prone segment. For example, a variant immunoglobulin may comprise a VH domain with a substitution at position 20 and a VL domain with a substitution at position 18. For example, the residue at position 20 in the VH domain may be substituted for A and the residue at position 18 in the VL domain may be substituted for V. For example, an immunoglobulin may comprise a VL domain with T18V substitution and a VH domain with a R20A or R20V substitution.

A variant immunoglobulin may comprise a VL domain which comprises a substitution in the VL position 45 aggregation-prone segment and a VH domain which comprises one or more substitutions in the VH position 75 aggregation-prone segment. For example, a variant immunoglobulin may comprise a VH domain with a substitution at position 61 and 85 and a VL domain with a substitution at position 46. For example, the residue at position 61 in the VH domain may be substituted for K, R, Q, E, D, N and A, preferably R, the residue at position 85 in the VH domain may be substituted for E, D, or A, preferably E, and the residue at position 46 in the VL domain may be substituted for K, R, H, F, or S, preferably R. For example, an immunoglobulin may comprise a VL domain with a L46R substitution and a VH domain with P61R and V85E substitutions.

A variant immunoglobulin may comprise a VL domain which comprises a substitution in the VL position 45 aggregation-prone segment and a VH domain which comprises one or more substitutions in the VH position 95 aggregation-prone segment and one or more substitutions in the VH CDR3 aggregation-prone segment. For example, a variant immunoglobulin may comprise a VH domain with substitutions at positions 95 and 102 and a VL domain with substitutions at positions 37 and 45. For example, the residue at position 95 in the VH domain may be substituted for E or D, preferably D, the residue at position 102 in the VH domain may be substituted for A, F, H, I, L, V or Y, preferably Y; the residue at position 37 in the VL domain may be substituted for Q or N, preferably Q; and the residue at position 45 in the VL domain may be substituted for R, K or E, preferably R. For example, an immunoglobulin may comprise a VL domain with L37Q and Q45R substitutions and a VH domain with R95D and S102V substitutions.

A variant immunoglobulin may comprise a VL domain which comprises a substitution in the VL position 45 aggregation-prone segment and a VH domain which comprises one or more substitutions in the VH position 95 aggregation-prone segment. For example, a variant immunoglobulin may comprise a VH domain with a substitution at position 94 and 95 and a VL domain with a substitution at position 46. For example, the residue at position 94 in the VH domain may be substituted for R, K or T, preferably R, the residue at position 95 in the VH domain may be substituted for E or D, preferably D, and the residue at position 46 in the VL domain may be substituted for K, R, H, F, or S, preferably R. For example, an immunoglobulin may comprise a VL domain with a L46R substitution and a VH domain with H94R and R95D substitutions.

The techniques required to make substitutions within amino acid sequences of aggregation-prone segments of VH, VL and CH1 domains are generally available in the art. For example, nucleic acid encoding the variant immunoglobulin comprising one or more substitutions may be produced using standard techniques of DNA manipulation and mutagenesis; for example as described in *Current Protocols in Molecular Biology*, Second Edition, Ausubel et al. eds., John Wiley & Sons, 1992 or *Molecular Cloning: a Laboratory Manual*: 2nd edition, Sambrook et al., 1989, Cold Spring Harbor Laboratory Press. The nucleic acid may then be expressed to produce the variant immunoglobulin, as described below.

Variant sequences may be tested for ability to bind and/or neutralize the target antigen of the parent immunoglobulin and/or for improved manufacturability.

The introduction of one or more of the substitutions set out above may increase the manufacturability of an variant immunoglobulin relative to its parent immunoglobulin by both increasing the productivity upon expression and reducing the aggregation-propensity of the variant immunoglobulin relative to its parent immunoglobulin.

For example, a variant immunoglobulin may display an increase in productivity of at least 10%, at least 20%, at least 30%, at least 40%, at least 50%, at least 100%, at least 200%, or at least 500% relative to the parent immunoglobulin and a decrease in aggregation of at least 10%, at least 20%, at least 30%, at least 40%, at least 50%, at least 80%, at least 90% or at least 99% relative to the parent immunoglobulin. A variant immunoglobulin may display a decrease in aggregation of up to 100% relative to the parent immunoglobulin (i.e. complete abolition of aggregation).

A method of producing a variant immunoglobulin as described herein may comprise providing a parent immunoglobulin, introducing a substitution in the VL domain at the VL position 37 aggregation-prone segment and/or the VL position 45 aggregation-prone segment and/or
  introducing a substitution in the VH domain at the VH FR1 aggregation-prone segment; the VH position 95 aggregation-prone segment; and the VH CDR3 aggregation-prone segment,
  thereby producing a variant immunoglobulin, wherein the variant immunoglobulin displays both increased productivity and reduced aggregation relative to the parent immunoglobulin.

For example, a method of producing a variant immunoglobulin may comprise;
  providing a parent immunoglobulin,
  introducing one or more substitutions A, D, E, Q or V at position 1, R at position 17; R at position 94; D at position 95; A at position 96; F at position 100; F, G, L, M or P, preferably F or M at position 100d; A, F, H, I, L, V or Y, preferably V or Y, at position 102 of the VH domain; and/or, introducing a substitution Q at position 37; E, K, R, Q or V, preferably K or R, at position 45; L or Y, preferably L, at position 46, of the VL domain;

thereby producing a variant immunoglobulin, wherein the variant immunoglobulin displays both increased productivity and reduced aggregation relative to the parent immunoglobulin.

For example, a suitable VH domain may have substitutions at positions 94 and 102 as described above, optionally with further substitutions at positions 94 and 100. For example, the residue at position 95 in the VH domain may be substituted for D, and the residue at position 102 may be substituted for A, F, H, I, L, V or Y, preferably V or Y; optionally, the residue at position 94 may also be substituted for R and the residue at position 100 substituted for F.

A suitable VL domain may have substitutions at positions 37 and 45 as described above. For example, the residue at position 37 may be substituted for Q and the residue at position 45 may be substituted for E, K, R, Q or V, preferably K or R. A VL domain may, for example, comprise L37Q and Q45R substitutions.

A variant immunoglobulin may comprise a VH domain with substitutions at positions 94 and 95 as described above and a VL domain with a substitution at position 46. For example, the residue at positions 94 and 95 in the VH domain may be substituted for R and D respectively and the residue at position 46 in the VL domain may be substituted for R. For example, an immunoglobulin may comprise a VL domain with L46R substitution and a VH domain with H94R and R95D substitutions.

Other variant immunoglobulins may comprise a VH domain with substitutions at positions 95 and 102 as described above and a VL domain with substitutions at positions 37 and 45. For example, the residues at positions 95 and 102 in the VH domain may be substituted for D and V respectively and the residues at position 37 and 45 in the VL domain may be substituted for Q and R respectively. For example, an immunoglobulin may comprise a VL domain with L73Q and Q45R substitutions and a VH domain with R95D and S102V substitutions.

The presence of aggregation-prone segments as described herein may be helpful in identifying immunoglobulins which display reduced or sub-optimal manufacturability.

A method of assessing the manufacturability of an immunoglobulin may comprise;

identifying the amino acid residue at one or more positions selected from the group consisting of positions 18, 20, 45, 46, 74, 91, 93 and 96 in the VL domain of the immunoglobulin and positions 1, 5, 12, 17, 19, 20, 94, 96, 100c, 100d, 102, 103 in the VH domain of the immunoglobulin, and position 153 in the CH1 domain, wherein the presence of a residue other than R, S or V, preferably R or V at position 18, K, R, S or V, preferably R or V at position 20, E, K, R, Q or V, preferably K or R, at position 45, L or Y, preferably L, at position 46, V at position 74, A, F, L, R, S, or W, preferably W at position 91, D, F, L, Q, S, T, W or Y, preferably Q, at position 93 and/or E, L, V or W, preferably V, at position 96 in the VL domain of the immunoglobulin and/or;

the presence of a residue other than A, D, E, Q or V at position 1, V at position 5 or position 12, R at position 17, T or V, preferably T at position 19, A, K, S or T, preferably A, at position 20, R at position 94, A at position 96, D, E, F, G, P, S, T, W, or Y, preferably W at position 100c, F, G, L, M or P, preferably F or M at position 100d, A, F, H, I, L, V or Y, preferably V or Y, at position 102, I, L or V at position 103 in the VH domain, and/or V at position 153 in the CH1 domain of the immunoglobulin is indicative that the immunoglobulin has sub-optimal manufacturability.

In some embodiments, the identity of the amino acid residue at position 100d and/or 102, in the VH domain of the immunoglobulin may be determined. The presence of a residue other than F, G, L, M or P, preferably F or M at position 100d, and/or a residue other than A, F, H, I, L, V or Y, preferably V or Y, at position 102 is indicative that the manufacturability of the immunoglobulin is sub-optimal.

An immunoglobulin whose manufacturability is identified as being reduced or sub-optimal relative to control immunoglobulins may be a candidate for modification by a method described above to produce a variant immunoglobulin which displays improved manufacturability.

In particular, one or more residues within an immunoglobulin sequence which have a deleterious effect on manufacturability may be identified. The identified residues may then be altered or modified as described herein to improve manufacturability.

Another aspect of the invention provides a variant of a parent immunoglobulin which is produced by a method set out above.

Another aspect of the invention provides a variant of a parent immunoglobulin;

wherein said variant immunoglobulin comprises;

a VL domain comprising a substitution at framework aggregation-prone segment and/or a CDR3 aggregation-prone segment relative to the sequence of the parent immunoglobulin;

a VH domain comprising a substitution at a framework aggregation-prone region and/or a CDR3 aggregation-prone segment relative to the sequence of the parent immunoglobulin; and/or, a CH1 domain comprising a substitution at a CH1 aggregation-prone region relative to the sequence of the parent immunoglobulin.

Suitable aggregation-prone segments and substitutions are described above.

A substitution at a position in the VL, VH, or CH1 domain, involves the replacement of the residue at the position in the parent sequence with a different residue, preferably a residue set out above. Where the parent immunoglobulin already contains a residue as set out above at the appropriate position in the amino acid sequence, this is not a substitution or a substituted residue as described herein. Parent or germ-line immunoglobulins are therefore not variant immunoglobulins as described herein.

As described above, a variant immunoglobulin may possess similar or identical biological activity to the parent immunoglobulin but display improved manufacturability, for example reduced aggregation propensity, and/or increased productivity in a heterologous expression system.

For example, a variant immunoglobulin may display an increase in productivity of at least 10%, at least 20%, at least 30%, at least 40%, at least 50%, at least 100%, at least 200%, or at least 500% relative to the parent immunoglobulin and/or a decrease in aggregation (i.e. a reduction in the proportion of molecules in the native state ensemble which are aggregated) of at least 10%, at least 20%, at least 30%, at least 40%, at least 50%, at least 80%, at least 90% or at least 99% relative to the parent immunoglobulin. A variant immunoglobulin may display a decrease in aggregation of up to 100% relative to the parent immunoglobulin (i.e. complete abolition of aggregation).

As described above, a variant immunoglobulin may display improved bioavailability and/or reduced immunogenicity relative to the parent immunoglobulin.

Another aspect of the invention provides an isolated nucleic acid encoding a variant immunoglobulin as described above or a CH1, VH or VL domain thereof.

Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A variant immunoglobulin molecule as described herein or a CH1, VH domain and/or a VL domain thereof may be prepared by a method which comprises expressing said nucleic acid under conditions to bring about production of said variant immunoglobulin molecule or CH1, VH and/or VL domain thereof, and recovering it.

As described in more detail below, a nucleic acid may encode a variant immunoglobulin or a VH or VL domain thereof which lacks one or more CDRs. One or more CDRs taken from a donor immunoglobulin may be incorporated into the framework of the variant immunoglobulin by inserting suitable nucleic acid encoding the CDR(s) into the nucleic acid encoding the variant immunoglobulin or a VH or VL domain thereof.

Variant immunoglobulins and encoding nucleic acid are preferably isolated. Immunoglobulins and nucleic acid will be free or substantially free of material with which they are associated such as other polypeptides or nucleic acids with which they are found in the environment in which they are prepared (e.g. cell culture) when such preparation is by recombinant DNA technology practised in vitro or in vivo.

Other aspects of the invention provide nucleic acid constructs in the form of plasmids, vectors, transcription or expression cassettes which comprise at least one nucleic acid encoding a variant immunoglobulin as described herein or a CH1, VH and/or VL domain thereof.

A construct may be used in an expression system in order to express an immunoglobulin as described above.

Systems for cloning and expression of immunoglobulins in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells and many others. A common, preferred bacterial host for small immunoglobulin molecules is E. coli.

The expression of immunoglobulins, such as antibodies and antibody fragments, in prokaryotic cells such as E. coli is well established in the art. For a review, see for example Plückthun, A. Bio/Technology 9: 545-551 (1991). Expression in eukaryotic cells in culture is also available to those skilled in the art as an option for production of a immunoglobulin, see for recent reviews, for example Ref, M. E. (1993) Curr. Opinion Biotech. 4: 573-576; Trill J. J. et al. (1995) Curr. Opinion Biotech 6: 553-560. Immunoglobulins, such as antibodies and antibody fragments, may also be expressed in cell-free systems.

Suitable vectors for the expression of immunoglobulins can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992.

Nucleic acid encoding a variant immunoglobulin or a CH1, VH and/or VL domain thereof may be contained in a host cell. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

Nucleic acid encoding the variant immunoglobulin or CH1, VH and/or VL domain thereof may be integrated into the genome (e.g. chromosome) of the host cell. Integration may be promoted by inclusion of sequences which promote recombination with the genome, in accordance with standard techniques.

Following production by expression, a variant immunoglobulin or CH1, VH and/or VL domain thereof may be isolated and/or purified using any suitable technique, then used as appropriate. For example, a method of production may further comprise formulating the product into a composition including at least one additional component, such as a pharmaceutically acceptable excipient.

Variant immunoglobulins may be used in a method of treatment or diagnosis of the human or animal body, such as a method of treatment (which may include prophylactic treatment) of a disease or disorder in a human patient which comprises administering to said patient an effective amount of the variant immunoglobulin.

Other aspects of the invention provide pharmaceutical compositions comprising a variant immunoglobulin as described herein, methods of making a medicament or pharmaceutical composition comprising formulating the variant immunoglobulin with a pharmaceutically acceptable excipient, and the use of a variant immunoglobulin in the manufacture of a medicament for administration.

In addition to the variant immunoglobulin, pharmaceutical compositions may comprise a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringers Injection, Lactated Ringers Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

Clinical indications in which a variant immunoglobulin may be used to provide therapeutic benefit include any condition or disorder for which the parent immunoglobulin may be useful.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will typically be in the range 0.5 mg to 1 g for systemic applications, and 10 µg to 1 mg for local applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Variant immunoglobulins which include substitutions within aggregation-prone segments and encoding nucleic acids as described herein may be useful in methods of antibody engineering to produce immunoglobulins with improved manufacturability.

Recombinant DNA technology may be used to produce variant immunoglobulins that possess the improved manufacturability. Such techniques may involve introducing DNA encoding one or more CDR sequences of a donor antibody to the variable region of a variant immunoglobulin as described herein. See, for instance, EP-A-184187, GB 2188638A or EP-A-239400, and a large body of subsequent literature. Alternatively, a hybridoma or other cell producing an immunoglobulin may be subject to genetic mutation within the sequences encoding the aggregation-prone segments of the immunoglobulin which improve the manufacturability of the immunoglobulin produced. This may be useful in engineering or re-formatting antibodies with manufacturability suitable for recombinant production.

In some embodiments, the VH and VL domains of the variant immunoglobulin may lack one or more CDR sequences (e.g. CDR3). Heterologous or synthetic CDRs may be introduced into the variant immunoglobulin VH and/or VL domains lacking the corresponding CDR (e.g. CDR3), using recombinant DNA technology. This may alter the binding properties of the variant immunoglobulin without affecting the manufacturability.

For example, one or more CDR sequences (e.g. CDR3) from a donor immunoglobulin may be used to replace the corresponding CDR sequences in a variant immunoglobulin as described herein. 1, 2, 3, 4, 5, or all 6 CDR sequences from a human variant immunoglobulin as described herein may be replaced by CDR sequences taken from a non-human donor immunoglobulin, such as a murine immunoglobulin, to produce a humanised immunoglobulin. A humanised immunoglobulin may possess the same binding activity as the non-human donor immunoglobulin but display reduced immunogenicity in a human and may therefore have therapeutic utility.

A method of preparing a hybrid immunoglobulin which binds to a target antigen may comprise;
  providing a donor immunoglobulin which binds to said target antigen,
  providing a variant immunoglobulin as described above, and;
  replacing 1, 2, 3, 4, 5 or 6 CDR sequences of said variant immunoglobulin with the corresponding CDR sequence from said donor immunoglobulin,
  thereby producing a hybrid immunoglobulin which binds said target antigen.

Preferably the VH CDR3 and/or VL CDR3 of the variant immunoglobulin are replaced with the corresponding VH CDR3 and/or VL CDR3 from the donor immunoglobulin.

The variant immunoglobulin may be a human immunoglobulin and the donor immunoglobulin may be a non-human immunoglobulin.

Suitable techniques for humanizing immunoglobulins by CDR grafting are well-known in the art (see for example, Riechman et al (1988) Nature 332 323-327; Queen et al PNAS USA (1989) 86 10029-10033).

The VL CDR3 of the hybrid immunoglobulin may comprise a substitution in the VL CDR3 N terminal aggregation-prone segment or the VL CDR3 C terminal aggregation-prone segment as described above.

The VH CDR3 of the hybrid immunoglobulin may comprise a substitution in the VH CDR3 aggregation-prone segment, as described above.

Suitable variant immunoglobulins may comprise one or more substitutions in framework or constant regions, as described above.

In some embodiments, substitutions may be introduced into the donor VH and/or VL CDR3 sequences. Substitutions may be made before or after insertion into the variant immunoglobulin using standard techniques.

Variant immunoglobulins as described herein may also be useful in methods of humanisation other than CDR grafting. One or more substitutions as described herein may be introduced into an immunoglobulin during the production of a humanized antibody to improve its manufacturability. Humanization techniques which may be employed are well-known in the art (see for example Padlan et al Mol Immunol. (1991) 28 489-498).

Variant immunoglobulins as described herein may be useful in the production of libraries or repertoires for the isolation of binding specificities.

A method of preparing a variant immunoglobulin library may comprise;
  providing a population of variant immunoglobulins as described above, replacing 1, 2, 3, 4, 5 or 6 CDR sequences of said population of variant immunoglobulins with a repertoire of CDR sequences, thereby producing a variant immunoglobulin library.

The variant immunoglobulin library will contain a diverse repertoire of replacement CDR sequences in the same variant immunoglobulin background.

The library may be screened for a variant immunoglobulin which is specific for a target antigen.

In some preferred embodiments, the VH CDR3 of a population of variant immunoglobulins may be replaced by a repertoire of VH CDR3 sequences. For example, a method of preparing a variant immunoglobulin which binds to a target antigen may comprise:

(a) providing a starting population of nucleic acids encoding a VH domain which either include a CDR3 to be replaced or lack a CDR3 encoding region; wherein said VH domain comprises one or more substitutions in one or more aggregation-prone segments as described above, (b) combining said VH domain population with a population of donor nucleic acids encoding a repertoire of VH CDR3 amino acid sequences such that said donor nucleic acid is inserted into the CDR3 region in the VH domain population, so as to provide a product population of nucleic acids encoding repertoire of VH domains comprising said VH CDR3 sequences;

(c) expressing the nucleic acids of said product population;

(d) selecting an immunoglobulin specific for a target antigen; and (e) recovering said immunoglobulin or nucleic acid encoding it.

The population of nucleic acids encoding a VH domain may further comprise a nucleotide sequence encoding a CH1 domain which comprises one or more substitutions in a CH1 aggregation-prone segment as described above.

In the same way, a repertoire of VL CDR3 sequences may be combined with a population of nucleic acids encoding a VL domain comprising one or more substitutions in aggregation-prone segments as described herein, and which either includes a VL CDR3 to be replaced or lacks a VL CDR3 encoding region.

In addition to CDR3, repertoires of CDR1 and CDR2 sequences may also be grafted into a population of VH and/or VL domains comprising one or more substitutions in aggregation-prone segments as described herein which are then screened for variant immunoglobulins specific for target antigen.

Repertoires of CDR-derived sequences may be shuffled with populations of VH or VL domains as described herein which lack the corresponding CDR sequence, and the shuffled complete VH or VL domains combined with a cognate VL or VH domain (which may also comprise one or more substitutions as described herein) to provide engineered variant immunoglobulins. The repertoire may then be displayed in a suitable host system such as the phage display system of WO92/01047 so that suitable immunoglobulins which possess improved manufacturability may be selected. A repertoire may consist of from anything from $10^4$ individual members upwards, for example from $10^6$ to $10^8$ or $10^{10}$ members.

Techniques of CDR shuffling and antibody engineering are well known in the art and the skilled person will be able to use such techniques to provide immunoglobulins with improved manufacturability using routine methodology.

A repertoire of CDR sequences may include a diversity of residues at one or more positions within the CDR sequence.

For example, a repertoire of CDR sequences may include a diversity of residues at 1, 2, 3, 4, 5 or more positions within the CDR sequence.

The repertoire of CDR sequences may include one or more variable positions within the CDR sequence. For example, a repertoire of CDR sequences may include 1, 2, 3, 4, 5 or more variable positions within the CDR sequence. The residue at each variable position may differ between different members of the repertoire. The residue at a variable position may be random (e.g. it may be any naturally occurring amino acid with equal probability) or may be selected from a predetermined group or subset of amino acids. For example, the VL CDR3 of the variant immunoglobulin may be replaced by a repertoire of donor VL CDR3 sequences which comprise A, F, L, R, S and W at position 91, D, F, L, Q, S, T, W and Y at position 93, and/or E, L, V and W at position 96. The VH CDR3 of the variant immunoglobulin may be replaced by a repertoire of donor VH CDR3 sequences which comprise D, E, F, G, P, S, T, W, and Y at position 100c, F, G, L, P and M at position 100d, A, F, H, I, L, V and Y at position 102, and/or I, L and V at position 103.

Biasing the CDR3 repertoires to these residues at these positions may be helpful in improving manufacturability.

In addition to one or more variable positions, the repertoire of CDR sequences may also include one or more non-variable positions. The residue at each non-variable position may be the same in each member of the repertoire.

Incorporation of a repertoire of CDR sequences into a recipient variant immunoglobulin may be useful in producing a library of variant immunoglobulins with diverse binding properties, with each member of the library comprising one or more substitutions in one or more aggregation-prone segments as described herein.

A variant immunoglobulin library may comprise;

a VL domain comprising a substitution at a framework aggregation-prone segment and/or a CDR3 aggregation-prone region as described above;

a VH domain comprising a substitution at a framework aggregation-prone region and/or a CDR3 aggregation-prone segment as described above; and/or, a CH1 domain comprising a substitution at a CH1 aggregation-prone region as described above;

wherein the members of the library differ in one or more CDR sequences.

A library of variant immunoglobulins may be useful in identifying immunoglobulins with improved manufacturability which are able to bind a target antigen. A method of obtaining one or more immunoglobulins which bind a target antigen may comprise;

bringing into contact a library of immunoglobulins as described above and said antigen, and selecting one or more immunoglobulins of the library able to bind said antigen.

The library may, for example, be displayed on the surface of bacteriophage particles, each particle containing nucleic acid encoding the antibody VH variable domain displayed on its surface, and optionally also a displayed VL domain if present.

Following selection of immunoglobulins able to bind the antigen and displayed on bacteriophage particles, nucleic acid may be taken from a bacteriophage particle displaying a said immunoglobulin. Such nucleic acid may be used in subsequent production of an immunoglobulin or an antibody VH variable domain and/or VL domain thereof by expression from nucleic acid with the sequence of nucleic acid taken from a bacteriophage particle displaying a said immunoglobulin.

The immunoglobulin may be tested for ability to bind antigen; compete with other immunoglobulins for binding to antigen and/or ability to neutralise antigen. Binding affinity and neutralisation potency of different immunoglobulins can be compared under appropriate conditions. The manufacturability of the immunoglobulin may also be tested.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the tables described below.

Tables 1a and 1b show the correspondence between Kabat and Honegger numbering schemes for immunoglobulin VH and VL domains.

Tables 2a and 2b show examples of amino acid substitutions within aggregation-prone segments which improve manufacturability. Preferred substitutions are also indicated. The standard IUPAC-IUB JCBN one-letter nomenclature for amino acids is used.

Tables 3a and 3b show examples of combinations of substitutions within aggregation-prone segments which improve manufacturability.

Table 4 shows the manufacturability of examples of variant immunoglobulins.

EXPERIMENTS

Gene Synthesis

Sequences were optimised and synthesised by a commercial supplier, and sub-cloned into pEE6.4 and pEE12.4. DNA stocks were prepared by transformation into Top10 cells, cultured O/N in LB broth and purified using QIAGEN Endofree plasmid purification kit. DNA was resuspended in TE buffer and the concentration determined using a Nanodrop spectrophotometer.

Routine Cell Culture

CHOK1SV cells were sub-cultured every 3-4 days in CD-CHO media supplemented with 15 mM L-Glutamine, and incubated in shaking $CO_2$ incubator (140 rpm), 36.5° C., 10% $CO_2$, 85% humidity.

Transient Transfections

CHOK1SV cells were transfected using Lipofectamine 2000. 72 h post-transfection, supernatants were harvested, centrifuged and stored at 4° C. prior to analysis.

Stable Transfections

Large scale expression was carried out using stably transfected CHOK1SV cells under MSX selection. Once harvested, supernatants were stored at 4° C. prior to purification.

Purification

Supernatants were Protein A purified using HiTrap columns (GE) and stored at 4° C. prior to concentration and buffer exchange.

Antibody Concentration and Buffer Exchange

Samples were concentrated by centrifugation at 2000 g 15-20 min. Material was buffer exchanged 4-5 times using formulation buffer (50 mM Phosphate, 100 mM NaCl, pH7.4). Once buffer exchanged, samples were diluted in formulation buffer to an appropriate working concentration.

GP-HPLC

Duplicate samples were analysed by GP-HPLC on an Agilent 1200 series HPLC system. 80 µl aliquots of 1 mg/ml samples (kept at 4° C.) were injected and run at 1 ml/min for 15 min. Results were analysed using chemstation software.

IgG Titre

Antibody expression yields were determined using a sandwich ELISA. Titres were normalised to a light chain specific control.

Thioflavin T Binding

Thioflavin T can be used to monitor aggregation. Purified antibody at 1 mg/ml was incubated at 60° for 1 h then mixed with a final concentration of 30 µM Thioflavin T, and fluorescence measured at Ex=305 Em=508 nm (Hawe, A., Sutter, M and Jiskoot, W. Pharmaceutical Research 2008 25 (7) 1487-99).

ANS Binding

8-Anilino-1-napthalenesulfonic acid (ANS) can be used to monitor aggregation. Purified antibody at 1 mg/ml was incubated at 60° for 1 h then mixed with a final concentration of 30 µM ANS and fluorescence measured at Ex=360 Em/508 nm (Hawe, A., Sutter, M and Jiskoot, W. Pharmaceutical Research 2008 25 (7) 1487-99).

Results

Immunoglobulin sequences were analysed by in silico and in vitro methods to identify aggregation prone segments. The identified aggregation-prone segments are shown in Table 2.

Substitutions within the identified aggregation prone segments of the VH and VL domains shown in SEQ ID NOS: 1 and 2 which reduced aggregation propensity were designed and synthesised (Table 2). The effect of the substitutions on expression, stability and aggregation of the immunoglobulin were tested (Tables 3 and 4).

The substitution of residues within the identified aggregation prone segments was found to result in an improvement in manufacturability, and in particular, in reduced aggregation propensity, and/or improved production levels.

Additional Numbered Statements of Invention

1. A variant immunoglobulin comprising;
    a light chain variable (VL) domain which comprises a substitution at framework (FR) aggregation-prone segment and/or a complementary determining region 3 (CDR3) aggregation-prone segment;
    a heavy chain variable (VH) domain which comprises a substitution at a framework region aggregation-prone segment and/or a CDR3 aggregation-prone segment; and/or,
    a heavy chain constant region 1 (CH1) domain which comprises a substitution at a CH1 aggregation-prone segment.

2. A method of improving the manufacturability of an immunoglobulin, comprising;
    identifying a parent immunoglobulin,
    introducing a substitution into a framework aggregation-prone segment and/or a CDR3 aggregation-prone segment in the VL domain of the parent immunoglobulin, and/or
    introducing a substitution into a framework region aggregation-prone segment and/or a CDR3 aggregation-prone segment in the VH domain of the parent immunoglobulin, and/or;
    introducing a substitution into a constant region aggregation-prone segment in the CH1 domain of the parent immunoglobulin, thereby producing a variant immunoglobulin having improved manufacturability relative to the parent immunoglobulin.

3. A variant immunoglobulin or a method according to any one of the preceding statements wherein the variant immunoglobulin has reduced aggregation propensity and/or increased productivity upon expression, relative to the parent immunoglobulin 4. A variant immunoglobulin or a method according to any one of the preceding statements wherein the VL domain framework aggregation-prone segment is selected from the group consisting of the position 20 aggregation-prone segment, the position 45 aggregation-prone segment and the position 74 aggregation-prone segment.

5. A variant immunoglobulin or a method according to statement 4 wherein the position 20 aggregation-prone segment extends from positions 15 to 23 of the VL domain.

6. A variant immunoglobulin or a method according to statement 5 wherein the VL domain comprises a substitution at position 18 of the VL domain.

7. A variant immunoglobulin or a method according to statement 6 wherein the residue at position 18 is substituted for R, S or V.

8. A variant immunoglobulin or a method according to statement 7 wherein the VL domain comprises a T18R, T18S or T18V.

9. A variant immunoglobulin or a method according to any one of statements 5 to 8 wherein the VL domain comprises a substitution at position 20 of the VL domain.

10. A variant immunoglobulin or a method according to statement 9 wherein the residue at position 20 is substituted for K, R, S or V.

11. A variant immunoglobulin or a method according to statement 10 wherein the VL comprises a T20K, T20R, T20S or T20V substitution.

12. A variant immunoglobulin or a method according to any one of statements 4 to 11 wherein the position 45 aggregation-prone segment extends from position 42 to position 49 of the VL domain.

13. A variant immunoglobulin or a method according to statement 12 wherein the VL domain comprises a substitution at position 45.

14. A variant immunoglobulin or a method according to statement 13 wherein the residue at position 45 is substituted for E, K, R, Q or V.

15. A variant immunoglobulin or a method according to statement 14 wherein the VL domain comprises a T45E, T45K, T45R, T45Q or T45V substitution.

16. A variant immunoglobulin or a method according to any one of statements 12 to 15 wherein the VL domain comprises a substitution at position 46.

17. A variant immunoglobulin or a method according to statement 16 wherein the residue at position 46 is substituted for L or Y.

18. A variant immunoglobulin or a method according to statement 17 wherein the VL domain comprises a T46L or T46Y substitution.

19. A variant immunoglobulin or a method according to any one of statements 4 to 18 wherein the position 74 aggregation-prone segment extends from position 71 to position 77 of the VL domain sequence.

20. A variant immunoglobulin or a method according to statement 19 wherein the VL domain comprises a substitution at position 74.

21. A variant immunoglobulin or a method according to statement 20 wherein the residue at position 74 is substituted for V.

22. A variant immunoglobulin or a method according to statement 21 wherein the VL domain comprises a T74V substitution.

23. A variant immunoglobulin or a method according to any one of the preceding statements wherein the VL domain CDR3 aggregation-prone segment is selected from the group consisting of the VL CDR3 N terminal aggregation-prone segment and the VL CDR3 C terminal aggregation-prone segment.

24. A variant immunoglobulin or a method according to statement 23 wherein the VL CDR3 N terminal aggregation-prone segment extends from residue C88 to the position eight amino acids C-terminus of residue C88 in the VL domain sequence.

25. A variant immunoglobulin or a method according to statement 24 wherein the VL domain comprises a substitution at one or more of positions 88, 89, 90, 91, 92, 93, 94, 95 or 95a.

26. A variant immunoglobulin or a method according to statement 25 wherein the VL domain comprises a substitution at position 91.

27. A variant immunoglobulin or a method according to statement 26 wherein the residue at position 91 is substituted for A, F, L, R, S or W.

28. A variant immunoglobulin or a method according to statement 27 wherein the VL domain comprises a Y91A, Y91F, Y91L, Y91R, Y91S or Y91W substitution.

29. A variant immunoglobulin or a method according to any one of statements 24 to 29 wherein the VL domain comprises a substitution at position 93.

30. A variant immunoglobulin or a method according to statement 29 wherein the residue at position 93 is substituted for D, F, L, Q, S, T, W or Y.

31. A variant immunoglobulin or a method according to statement 30 wherein the VL domain comprises a P93D, P93F, P93L, P93Q, P93S, P93T, P93W or P93Y substitution.

32. A variant immunoglobulin or a method according to statement 23 wherein the VL C terminal CDR3 aggregation-prone segment extends from the position three amino acids N-terminal of residue F98 to position 99 in the VL domain sequence.

33. A variant immunoglobulin or a method according to statement 32 wherein the VL domain comprises a substitution at one or more of positions 95, 96, 97, 98 or 99.

34. A variant immunoglobulin or a method according to statement 33 wherein the VL domain comprises a substitution at position 96.

35. A variant immunoglobulin or a method according to statement 34 wherein the residue at position 96 is substituted for E, L, V or W.

36. A variant immunoglobulin or a method according to statement 35 wherein the VL domain comprises a R96E, R96L, R96V or R96W substitution.

37. A variant immunoglobulin or a method according to any one of the preceding statements wherein the VH domain framework aggregation-prone segment is selected from the group consisting of the FR1 aggregation-prone segment; the position 95 aggregation-prone segment; and the position 102 aggregation-prone segment.

38. A variant immunoglobulin or a method according to statement 37 wherein the FR1 aggregation-prone segment is located in framework region 1 of the VH domain sequence.

39. A variant immunoglobulin or a method according to statement 38 wherein the FR1 aggregation-prone segment is an aggregation-prone segment selected from the group consisting of positions 1 to 3; positions 4 to 6, positions 11 to 13, and positions 16 to 21.

40. A variant immunoglobulin or a method according to statement 39 wherein FR1 aggregation-prone segment extends from position 1 to position 3.

41. A variant immunoglobulin or a method according to statement 40 wherein the VH domain comprises a substitution at position 1 of the VH domain.

42. A variant immunoglobulin or a method according to statement 41 wherein the residue at position 1 is substituted for E, Q, D, A or V.

43. A variant immunoglobulin or a method according to statement 42 wherein the VH domain comprises a Q1E, Q1D, Q1A or Q1V substitution or an E1Q, E1D, E1A or E1V substitution.

44. A variant immunoglobulin or a method according to statement 39 wherein the FR1 aggregation-prone segment extends from position 4 to position 6 of the VH domain.

45. A variant immunoglobulin or a method according to statement 44 wherein the VH domain comprises a substitution at position 5 of the VH domain.

46. A variant immunoglobulin or a method according to statement 45 wherein the residue at position 5 is substituted for V.

47. A variant immunoglobulin or a method according to statement 46 wherein the VH domain comprises a L5V.

48. A variant immunoglobulin or a method according to statement 39 wherein the FR1 aggregation-prone segment extends from position 11 to position 13 of the VH domain.

49. A variant immunoglobulin or a method according to statement 48 wherein the VH domain comprises a substitution at position 12 of the VH domain.

50. A variant immunoglobulin or a method according to statement 49 wherein the residue at position 12 is substituted for V.

51. A variant immunoglobulin or a method according to statement 50 wherein the VH domain comprises a L12V.

52. A variant immunoglobulin or a method according to statement 39 wherein the FR1 aggregation-prone segment extends from position 16 to position 21 of the VH domain.

53. A variant immunoglobulin or a method according to statement 52 wherein the VH domain comprises a substitution at position 17.

54. A variant immunoglobulin or a method according to statement 53 wherein the residue at position 17 is substituted for R.

55. A variant immunoglobulin or a method according to statement 54 wherein the VH domain comprises a G17R substitution.

56. A variant immunoglobulin or a method according to any one of statements 52 to 55 wherein the VH domain comprises a substitution at position 19.

57. A variant immunoglobulin or a method according to statement 56 wherein the residue at position 19 is substituted for T or V.

58. A variant immunoglobulin or a method according to statement 57 wherein the VH domain comprises a L19T or and L19V substitution.

59. A variant immunoglobulin or a method according to any one of statements 52 to 58 wherein the VH domain comprises a substitution at position 20.

60. A variant immunoglobulin or a method according to statement 59 wherein the residue at position 20 is substituted for A, K, S or T.

61. A variant immunoglobulin or a method according to statement 60 wherein the residue at position wherein the VH domain comprises a R20A, R20K or R20S or R20T substitution.

62. A variant immunoglobulin or a method according to any one of statements 37 to 61 wherein the position 95 aggregation-prone segment extends from position 91 to position 99.

63. A variant immunoglobulin or a method according to statement 62 wherein the VH domain comprises a substitution at one or more of positions 91, 92, 93, 94, 95, 96, 97, 98 and/or 99.

64. A variant immunoglobulin or a method according to statement 63 wherein the VH domain comprises a substitution at position 94.

65. A variant immunoglobulin or a method according to statement 64 wherein the residue at position 94 is substituted for R.

66. A variant immunoglobulin or a method according to statement 65 wherein the VH domain comprises a K94R substitution.

67. A variant immunoglobulin or a method according to any one of statements 63 to 66 wherein the VH domain comprises a substitution at 96.

68. A variant immunoglobulin or a method according to statement 67 wherein the residue at position 96 is substituted for A.

69. A variant immunoglobulin or a method according to statement 68 wherein the VH domain comprises a G96A substitution.

70. A variant immunoglobulin or a method according to any one of statements 1 to 69 wherein the VH CDR3 aggregation-prone segment extends from the position 100c to position 103.

71. A variant immunoglobulin or a method according to statement 70 wherein the VH domain comprises a substitution at one or more of positions 100c, 100d, 101, 102 and 103.

72. A variant immunoglobulin or a method according to statement 71 wherein the VH domain comprises a substitution at position 100c.

73. A variant immunoglobulin or a method according to statement 72 wherein the residue at the position 100c is substituted for D, E, F, G, P, S, T, W, or Y.

74. A variant immunoglobulin or a method according to statement 73 wherein the VH domain comprises a A100cD, A100cE, A100cF, A100cG, A100cP, A100cS, A100cT, or A100cW or A100cY.

75. A variant immunoglobulin or a method according to any one of statements 70 to 74 wherein the VH domain comprises a substitution at position 100d.

76. A variant immunoglobulin or a method according to statement 75 wherein the residue at position 100d is substituted for F, G, L, P or M.

77. A variant immunoglobulin or a method according to statement 76 wherein the VH domain comprises a S100dF, S100dG, S100dL, S100dP or S100dM substitution.

78. A variant immunoglobulin or a method according to any one of statements 70 to 77 wherein the VH domain comprises a substitution at position 102.

79. A variant immunoglobulin or a method according to statement 78 wherein the residue at position 102 is substituted for A, F, H, I, L, V or Y.

80. A variant immunoglobulin or a method according to statement 79 wherein the VH domain comprises a P102A, P102F, P102H, P102I, P102L, P102Y or P102V substitution.

81. A variant immunoglobulin or a method according to any one of statements 70 to 80 wherein the VH domain comprises a substitution at position 103.

82. A variant immunoglobulin or a method according to statement 81 wherein the residue at position 103 is substituted for I, L or V.

83. A variant immunoglobulin or a method according to statement 82 wherein the VH domain comprises a W103I, W103L or W103V substitution.

84. A variant immunoglobulin or a method according to any one of statements 1 to 83 wherein the CH1 aggregation-prone segment extends from position 150 to position 156.

85. A variant immunoglobulin or a method according to statement 84 wherein the CH1 domain comprises a substitution at position 153.

86. A variant immunoglobulin or a method according to statement 85 wherein the CH1 domain comprises a substitution at position 153.

87. A variant immunoglobulin or a method according to statement 86 wherein the residue at position 153 is substituted for V.

88. A variant immunoglobulin or a method according to statement 87 wherein the VH domain comprises a S153V substitution.

89. A variant immunoglobulin or a method according to any one of the preceding statements wherein the sequence of the variant immunoglobulin has up to 10 amino acid substitutions relative to the parent immunoglobulin sequence.

90. A variant immunoglobulin or a method according to any one of the preceding statements wherein the sequence of the variant immunoglobulin comprises 2 substitutions in the VL FR1 and/or FR2 domain; 3 substitutions in the VL CDR3 domain; 2 substitutions in the VL FR2 domain and 3 substitutions in the VL CDR3 domain; 2 substitutions in the VL FR1 domain, 2 substitutions in the VL FR2 domain and 3 substitutions in the VL CDR3 domain; 2 substitutions in the VH FR1 domain; 1 substitution in the VH FR1 domain and 1 substitution in the VH CDR3 domain; 2 substitutions in the VH CDR3 domain; or 1 substitution in the CH1 domain and 1 substitution in the VH FR1 domain.

91. A variant immunoglobulin or a method according to statement 90 wherein the sequence of the VH domain comprises a 100d (D101-1) and a 102 substitution.

92. A variant immunoglobulin or a method according to statement 91 wherein the residue at position 102 is substituted for A, F, H, I, L, V or Y and wherein the residue at position 100d is substituted for F, G, L, P or M.

93. A variant immunoglobulin or a method according to statement 92 wherein the VH domain comprises a P102A, P102F, P102H, P102I, P102L, P102Y or P102V substitution and a S100dF, S100dG, S100dL, S100dP or S100dM substitution.

94. A variant immunoglobulin or a method according to statement 93 wherein the VH domain comprises S100dF and P102V substitutions, S100dM and P102V substitutions, S100dF and P102Y substitutions or S100dM and P102Y substitutions.

95. A variant immunoglobulin or a method according to any one of the preceding statements wherein the variant immunoglobulin is humanised.

96. A method of assessing the manufacturability of an immunoglobulin comprising;
identifying the amino acid residue at one or more positions selected from the group consisting of positions 18, 20, 45, 46, 74, 91, 93 and 96 in the VL domain of the immunoglobulin, positions 1, 5, 12, 17, 19, 20, 94, 96, 100c, 100d, 102, and 103, in the VH domain, and position 153 in the CH1 domain of the immunoglobulin,
wherein the presence of a residue other than R, S or V, preferably R or V at position 18, K, R, S or V, preferably R or V at position 20, E, K, R, Q or V, preferably K or R, at position 45, L or Y, preferably L, at position 46, V at position 74, A, F, L, R, S, or W, preferably W at position 91, D, F, L, Q, S, T, W or Y, preferably Q, at position 93 and/or E, L, V or W, preferably V, at position 96 in the VL domain of the immunoglobulin and/or;
the presence of a residue other than A, D, E, Q or V at position 1, V at position 5 or position 12, R at position 17, T or V, preferably T at position 19, A, K, S or T, preferably A, at position 20, R at position 94, A at position 96, D, E, F, G, P, S, T, W, or Y, preferably W at position 100c, F, G, L, M or P, preferably F or M at position 100d, A, F, H, I, L, V or Y, preferably V or Y, at position 102, I, L or V at position 103 in the VH domain of the immunoglobulin and/or
the presence of a residue other than V at position 153 in the CH1 domain of the immunoglobulin,
is indicative that the manufacturability of the immunoglobulin are sub-optimal.

97. A method of assessing the manufacturability of an immunoglobulin comprising;
identifying the amino acid residue at positions 100d and/or 102, in the VH domain of the immunoglobulin,
wherein the presence of a S at position 100d and/or P at position 102, is indicative that the immunoglobulin has sub-optimal manufacturability.

98. An isolated nucleic acid encoding a variant immunoglobulin according to any one of statements 1 to 95 or a VH domain, VL domain or CH1 domain thereof comprising one or more of said substitutions.

99. An expression vector comprising an isolated nucleic acid according to statement 98.

100. A host cell comprising an expression vector according to statement 99.

101. A method of preparing a variant immunoglobulin comprising;
expressing a nucleic acid according to statement 98 under conditions to bring about production of said variant immunoglobulin or a VH domain, VL domain or CH1 domain thereof, and recovering it.

102. A method according to statement 101 comprising formulating the variant immunoglobulin into a composition including a pharmaceutically acceptable excipient.

103. A pharmaceutical composition comprising a variant immunoglobulin according to any one of statements 1 to 95 and a pharmaceutically acceptable excipient.

104. A variant immunoglobulin according to any one of statements 1 to 95 for use as a medicament.

105. A method of preparing a hybrid immunoglobulin which binds to a target antigen comprising;
providing a donor immunoglobulin which binds to said target antigen,
providing a variant immunoglobulin according to any one of statements 1 to 89,
replacing 1 or more CDR sequences of said variant immunoglobulin with the corresponding CDR sequence from said donor immunoglobulin,
thereby producing a hybrid immunoglobulin which binds said target antigen.

106. A method according to statement 105 wherein the VL CDR3 of the hybrid immunoglobulin comprises a substitution in the VL CDR3 N terminal aggregation-prone segment or the VL CDR3 C terminal aggregation-prone segment.

107. A method according to statement 105 or statement 106 wherein the VH CDR3 of the hybrid immunoglobulin comprises a substitution in the VH CDR3 aggregation-prone segment.

108. A method of preparing a variant immunoglobulin library comprising;

providing a variant immunoglobulin according to any one of statements 1 to 95,
replacing 1 or more CDR sequences of said variant immunoglobulin with a CDR sequence comprising a random residue at one or more positions therein,
thereby producing a diverse library of variant immunoglobulins.

109. A method according to statement 108 wherein the VL CDR3 of the variant immunoglobulin is replaced by a random CDR3 sequence which comprises A, F, L, R, S or W at position 91, D, F, L, Q, S, T, W or Y at position 93, and/or E, L, V or W at position 96.

110. A method according to statement 108 or statement 109 wherein the VH CDR3 of the variant immunoglobulin is replaced by a random CDR3 sequence which comprises D, E, F, G, P, S, T, W, or Y at position 100c, F, G, L, P or M at position 100d, A, F, H, I, L, V or Y at position 102, and/or I, L or V at position 103.

111. A variant immunoglobulin library, wherein each member of the library comprises;
 a VL domain comprising a substitution at framework aggregation-prone segment and/or a CDR3 aggregation-prone segment;
 a VH domain comprising a substitution at a framework region aggregation-prone segment and/or a CDR3 aggregation-prone segment; and/or,
 a CH1 domain comprising a substitution at a CH1 aggregation-prone segment
 wherein the members of the library differ in one or more CDR sequences.

112. A population of nucleic acids which encodes a variant immunoglobulin library according to statement 111.

113. A method of obtaining one or more immunoglobulins with improved manufacturability which bind to a target antigen comprising;
 bringing into contact a variant immunoglobulin library according to statement 111 and said antigen, and selecting one or more immunoglobulins of the library able to bind said antigen.

Sequences:
VL
(SEQ ID NO: 1)
NFMLTQPHSVSESPGKTVTISCTRSSGSIASNYVQWYQQRPGSSPTTVIY

EDNQRPSGVPDRFSGSIDSSSNSASLTISGLKTEDEADYYCQSYDPEMRV

FGGGTKLTVL

VH
(SEQ ID NO: 2)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAKTY

EGPTYFASDPWGQGTLVTVSS

TABLE 1A

| VL domain numbering | | |
|---|---|---|
| Sequence B | Kabat | Honegger |
| N | 1 | 1 |
| F | 2 | 2 |
| M | 3 | 3 |
| L | 4 | 4 |
| T | 5 | 5 |
| Q | 6 | 6 |
| P | 7 | 7 |

TABLE 1A-continued

| VL domain numbering | | |
|---|---|---|
| Sequence B | Kabat | Honegger |
|  | 8 | 8 |
| H | 9 | 9 |
| S | 10 | 10 |
| V | 11 | 11 |
| S | 12 | 12 |
| E | 13 | 13 |
| S | 14 | 14 |
| P | 15 | 15 |
| G | 16 | 16 |
| K | 17 | 17 |
| T | 18 | 18 |
| V | 19 | 19 |
| T | 20 | 20 |
| I | 21 | 21 |
| S | 22 | 22 |
| C | 23 | 23 |
| T | 24 | 24 |
| R | 25 | 25 |
| S | 26 | 26 |
| S | 27 | 27 |
| G | 27a | 28 |
| S | 27b | 29 |
|  | 27c | 30 |
|  | 27d | 31 |
|  | 27e | 32 |
|  | 27f | 33 |
|  |  | 34 |
|  |  | 35 |
| I | 28 | 36 |
| A | 29 | 37 |
| S | 30 | 38 |
| N | 31 | 39 |
| Y | 32 | 40 |
| V | 33 | 41 |
| Q | 34 | 42 |
| W | 35 | 43 |
| Y | 36 | 44 |
| Q | 37 | 45 |
| Q | 38 | 46 |
| R | 39 | 47 |
| P | 40 | 48 |
| G | 41 | 49 |
| S | 42 | 50 |
| S | 43 | 51 |
| P | 44 | 52 |
| T | 45 | 53 |
| T | 46 | 54 |
| V | 47 | 55 |
| I | 48 | 56 |
| Y | 49 | 57 |
| E | 50 | 58 |
|  |  | 59 |
|  |  | 60 |
|  |  | 61 |
|  |  | 62 |
|  |  | 63 |
|  |  | 64 |
|  |  | 65 |
|  |  | 66 |
| D | 51 | 67 |
| N | 52 | 68 |
| Q | 53 | 69 |
| R | 54 | 70 |
| P | 55 | 71 |
| S | 56 | 72 |
| G | 57 | 73 |
| V | 58 | 74 |
| P | 59 | 75 |
| D | 60 | 76 |
| R | 61 | 77 |
| F | 62 | 78 |
| S | 63 | 79 |
| G | 64 | 80 |
| S | 65 | 81 |
| I | 66 | 82 |
| D | 67 | 83 |

TABLE 1A-continued

VL domain numbering

| Sequence B | Kabat | Honegger |
|---|---|---|
| S | 68 | 84 |
| S | 68a | 85 |
| S | 68b | 86 |
| N | 69 | 87 |
| S | 70 | 88 |
| A | 71 | 89 |
| S | 72 | 90 |
| L | 73 | 91 |
| T | 74 | 92 |
| I | 75 | 93 |
| S | 76 | 94 |
| G | 77 | 95 |
| L | 78 | 96 |
| K | 79 | 97 |
| T | 80 | 98 |
| E | 81 | 99 |
| D | 82 | 100 |
| E | 83 | 101 |
| A | 84 | 102 |
| D | 85 | 103 |
| Y | 86 | 104 |
| Y | 87 | 105 |
| C | 88 | 106 |
| Q | 89 | 107 |
| S | 90 | 108 |
| Y | 91 | 109 |
| D | 92 | 110 |
| P | 93 | 111 |
| E | 94 | 112 |
| M | 95 | 113 |
|  | 95a | 114 |
|  | 95b | 115 |
|  | 95c | 116 |
|  | 95d | 117 |
|  | 95e | 118 |
|  | 95f | 119 |
|  |  | 120 |
|  |  | 121 |
|  |  | 122 |
|  |  | 123 |
|  |  | 124 |
|  |  | 125 |
|  |  | 126 |
|  |  | 127 |
|  |  | 128 |
|  |  | 129 |
|  |  | 130 |
|  |  | 131 |
|  |  | 132 |
|  |  | 133 |
|  |  | 134 |
|  |  | 135 |
|  |  | 136 |
| R | 96 | 137 |
| V | 97 | 138 |
| F | 98 | 139 |
| G | 99 | 140 |
| G | 100 | 141 |
| G | 101 | 142 |
| T | 102 | 143 |
| K | 103 | 144 |
| L | 104 | 145 |
| T | 105 | 146 |
| V | 106 | 147 |
| L | 107 | 148 |

TABLE 1B

VH Domain numbering

| Sequence B | Kabat | Honegger |
|---|---|---|
| Q | 1 | 1 |
| V | 2 | 2 |
| Q | 3 | 3 |
| L | 4 | 4 |
| V | 5 | 5 |
| E | 6 | 6 |
| S | 7 | 7 |
|  | 8 | 8 |
| G | 9 | 9 |
| G | 10 | 10 |
| G | 11 | 11 |
| V | 12 | 12 |
| V | 13 | 13 |
| Q | 14 | 14 |
| P | 15 | 15 |
| G | 16 | 16 |
| R | 17 | 17 |
| S | 18 | 18 |
| L | 19 | 19 |
| R | 20 | 20 |
| L | 21 | 21 |
| S | 22 | 22 |
| C | 23 | 23 |
| A | 24 | 24 |
| A | 25 | 25 |
| S | 26 | 26 |
| G | 27 | 27 |
| F | 28 | 28 |
| T | 29 | 29 |
| F | 30 | 30 |
| S | 31 | 31 |
| S | 32 | 32 |
| Y | 33 | 33 |
| G | 34 | 34 |
| M | 35 | 35 |
| H | 35a | 36 |
|  | 35b | 37 |
|  |  | 38 |
|  |  | 39 |
|  |  | 40 |
|  |  | 41 |
|  |  | 42 |
| W | 36 | 43 |
| V | 37 | 44 |
| R | 38 | 45 |
| Q | 39 | 46 |
| A | 40 | 47 |
| P | 41 | 48 |
| G | 42 | 49 |
| K | 43 | 50 |
| G | 44 | 51 |
| L | 45 | 52 |
| E | 46 | 53 |
| W | 47 | 54 |
| V | 48 | 55 |
| A | 49 | 56 |
| V | 50 | 57 |
| I | 51 | 58 |
| S | 52 | 59 |
| Y | 52a | 60 |
|  | 52b | 61 |
|  | 52c | 62 |
|  |  | 63 |
| D | 53 | 64 |
| G | 54 | 65 |
| S | 55 | 66 |
| N | 56 | 67 |
| K | 57 | 68 |
| Y | 58 | 69 |
| Y | 59 | 70 |
| A | 60 | 71 |
| D | 61 | 72 |
| S | 62 | 73 |
| V | 63 | 74 |
| K | 64 | 75 |
| G | 65 | 76 |
| R | 66 | 77 |
| F | 67 | 78 |
| T | 68 | 79 |

TABLE 1B-continued

VH Domain numbering

| Sequence B | Kabat | Honegger |
|---|---|---|
| I | 69 | 80 |
| S | 70 | 81 |
| R | 71 | 82 |
| D | 72 | 83 |
| N | 73 | 84 |
| S | 74 | 85 |
| K | 75 | 86 |
| N | 76 | 87 |
| T | 77 | 88 |
| L | 78 | 89 |
| Y | 79 | 90 |
| L | 80 | 91 |
| Q | 81 | 92 |
| M | 82 | 93 |
| N | 82a | 94 |
| S | 82b | 95 |
| L | 82c | 96 |
| R | 83 | 97 |
| A | 84 | 98 |
| E | 85 | 99 |
| D | 86 | 100 |
| T | 87 | 101 |
| A | 88 | 102 |
| V | 89 | 103 |
| Y | 90 | 104 |
| Y | 91 | 105 |
| C | 92 | 106 |
| A | 93 | 107 |
| K | 94 | 108 |
| T | 95 | 109 |
| Y | 96 | 110 |
| E | 97 | 111 |
| G | 98 | 112 |
| P | 99 | 113 |
| T | 100 | 114 |
| Y | 100a | 115 |
| F | 100b | 116 |
| A | 100c | 117 |
| S | 100d | 118 |
|   | 100e | 119 |
|   | 100f | 120 |
|   | 100g | 121 |
|   | 100h | 122 |
|   | 100i | 123 |
|   |   | 124 |
|   |   | 125 |
|   |   | 126 |
|   |   | 127 |
|   |   | 128 |
|   |   | 129 |
|   |   | 130 |
|   |   | 131 |
|   |   | 132 |
|   |   | 133 |
|   |   | 134 |
|   |   | 135 |
|   |   | 136 |
| D | 101 | 137 |
| P | 102 | 138 |
| W | 103 | 139 |
| G | 104 | 140 |
| Q | 105 | 141 |
| G | 106 | 142 |
| T | 107 | 143 |
| L | 108 | 144 |
| V | 109 | 145 |
| T | 110 | 146 |
| V | 111 | 147 |
| S | 112 | 148 |
| S | 113 | 149 |

TABLE 2a

Substitution Positions

| Segment | Residues important for aggregation | Preferred variants | Variants Tested |
|---|---|---|---|
| LC | | | |
| A-light | T18 | R S V | R V |
| A-light | T20 | K R S V | R V |
| B-light | T45 | E K R Q V | K R |
| B-light | T46 | L Y | L |
| C-light | T74 | V | V |
| D-light | Y91 (C88+3)* | A F L R S W | W |
| D-light | P93 (C88+5)* | D F L Q S T W Y | Q |
| E-light | R96 (F98-2)* | E L V W | V |
| HC | | | |
| A-heavy | E1 | A D Q V | Q |
| A-heavy | Q1 | A D E V | A D E V |
| B-heavy | L5 | V | V |
| C-heavy | L12 | V | V |
| D-heavy | G17 | R | R |
| D-heavy | L19 | T V | T |
| D-heavy | R20 | A K S T | A |
| E-heavy | K94 | R | R |
| E-heavy | G96 | A | A |
| F-heavy | A100c (D101-2)** | D E F G P S T W Y | W |
| F-heavy | S100d (D101-1)** | F G L M P | F M |
| F-heavy | P102 | A F H I L V Y | V Y |
| F-heavy | W103 | I L V | I L V |
| G-heavy | S153 | V | V |

*VL CDR3 positions: Y91, P93 are also numbered by proximity to Kabat's C88 & R96 is also numbered by proximity to Kabat's F98 respectively
**VH CDR3 positions: Due to heterogeneity of CDR3 (heavy) Positions are also named according to proximity to D101 (invariable in Kabat)

TABLE 2b

Substitutions positions

| Segment | Residues important for aggregation | Preferred variants | Variants tested |
|---|---|---|---|
| LC | | | |
| B-light | L37 | Q N | Q |
| B-light | L46 | K R H F S | R |
| B-light | Q45 | R K E | R |
| HC | | | |
| D-heavy | P61 | K R Q E D N A | R |
| D-heavy | V85 | E D A | E |
| E-heavy | H94 | R K T | R |
| E-heavy | R95 | E D | D |
| E-heavy | V100 | F G L M P | F |
| E-heavy | S102 | A F H I L V Y | V |

TABLE 3a

| Variant combinations | Combinations Tested |
|---|---|
| LC | |
| T18 T20 | T18R T20R |
| T18 T74 | T18R T74V |
| T45 T46 | T45K T46L |
|   | T45R T46L |
|   | T18R T20R T45K T46L |
|   | T18R T20R T45K T46L |
| Y91 (C88+3)* P93 (C88+5)* R96 (F98-2)* | Y91W (C88+3)* P93Q (C88+5)* R96V (F98-2)* |
|   | T45K T46L Y91W (C88+3)* P93Q (C88+5)* R96V(F98-2)* |
|   | T45R T46L Y91W (C88+3)* P93Q (C88+5)* R96V (F98-2)* |

TABLE 3a-continued

| Variant combinations | Combinations Tested |
|---|---|
|  | T18R T20R T45R T46L Y91W (C88+3)* P93Q (C88+5)* R96V (F98-2)* |
| HC |  |
| Q1 P102 | Q1A P102Y |
|  | Q1E P102Y |
|  | Q1V P102Y |
| Q1 W103 | Q1A W103L |
|  | Q1D W103L |
|  | Q1E W103L |
|  | Q1V W103L |
| A100c (D101-2)** |  |
| S100d (D101-1)** | A100cW (D101-2)** S100dF (D101-1)** |
| S100d (D101-1)** |  |
| P102 | S100dF (D101-1)** P102V |
|  | S100dF (D101-1)** P102Y |
|  | S100dM (D101-1)**P102V |
|  | S100dM (D101-1)** P102Y |
| P102 W103 | P102V W103L |
|  | P102Y, W103L |
|  | P102Y W103I |
|  | P102Y W103V |
| S153 L19 | S153V L19T |
| S153 R20 | S153V R20A |
| LC & HC |  |
| T18 R20 | T18V R20A |
|  | T18V R20V |

*VL CDR3 positions: Y91, P93 are also numbered by proximity to Kabat's C88 & R96 is also numbered by proximity to Kabat's F98 respectively
**VH CDR3 positions: Due to heterogeneity of CDR3 (heavy) Positions are also named according to proximity to D101 (invariable in Kabat)

TABLE 3b

| Variant combinations | Combinations tested |
|---|---|
| HC |  |
| R95 S102 | R95D S102V |
| H94 R95 V100 S102 | H94R R95D V100F S102V |
| HC/LC |  |
| P61 V85/L46 | P61R V85E/L46R |
| R95 S102/L37 Q45 | R95D S102V/L37Q Q45R |
| H94 R95/L46 | H94R R95D/L46R |
| LC |  |
| L37 Q45 | L37Q Q45R |

TABLE 4

| Substitution made (Kabat numbering) | LC or HC | Rel. Aggregation | Rel. Productivity | Rel. Thioflavin T binding | Rel. ANS binding |
|---|---|---|---|---|---|
|  |  | 1 | 1 | 1 | 1 |
| T18V | LC | 0.28 | 0.43 | 0.49 | 0.35 |
| T74V | LC | 0.23 | 0.05 | 0.88 | 0.81 |
| T18V T74V | LC | 0.21 | 0.23 | 0.45 | 0.48 |
| L37Q Q45R | LC | 0.31 | 1.84 |  |  |
| L46R | LC | 0.4 | 1.4 |  |  |
| E1Q | HC | 0.51 | 6.73 |  |  |
| L5V | HC | 0.63 | 0.51 |  |  |
| L12V | HC | 0.92 | 0.92 |  |  |
| G17R | HC | 0.52 | 1.76 |  |  |
| L19T | HC | 0.52 | 0.53 | 0.87 | 1.16 |
| R95D | HC | 0.05 | 2.69 |  |  |
| R20A | HC | 0.61 | 0.57 | 1.22 | 1.33 |
| S153V | HC | 0.73 |  |  |  |
| S153V R20A | HC | 0.31 | 0.78 | 0.95 | 1.22 |
| S153V L19T | HC | 0.41 | 0.43 | 0.7 | 0.87 |
| T18V/R20A | LC/HC | 0.59 | 0.04 | 0.52 |  |
| T18V/R20V | LC/HC | 0.86 |  |  |  |
| L46R/H94R R95D | LC/HC | 0.14 | 2.33 |  |  |
| L46R/P61R V85E | LC/HC | 0.52 | 0.77 |  |  |
| L37Q Q45R/R95D S102V | LC/HC | 0.01 | 18.77 |  |  |
| G96A | HC | 0.69 | 4.38 |  |  |
| S102V | HC | 0.10 | 6.61 |  |  |
| P102Y | HC | 0.60 | 1.57 | 0 | 0.12 |
| Q1E | HC | 1.03 | 1.96 |  |  |
| Q1V | HC | 1.12 | 2.21 |  |  |
| Q1A | HC | 1.17 | 1.84 |  |  |
| Q1D | HC |  | 1.58 |  |  |
| S100dF (D101-1)** | HC | 1.26 | 2.64 |  |  |
| S100dM (D101-1)** | HC | 0.54 | 3.44 |  |  |
| P102Y | HC | 0.55 | 1.71 |  |  |
| P102V | HC | 0.39 | 1.37 |  |  |
| W103L | HC |  | 0.74 |  |  |
| W103V | HC |  | 1.37 |  |  |
| W103I | HC |  | 0.81 |  |  |
| Q1A P102Y | HC | 0.58 | 1.69 |  |  |
| Q1E P102Y | HC | 0.58 | 1.23 |  |  |
| Q1V P102Y | HC | 0.59 | 0.78 |  |  |
| Q1A W103L | HC |  | 0.76 |  |  |
| Q1D W103L | HC |  | 1.08 |  |  |
| Q1E W103L | HC |  | 0.99 |  |  |
| Q1V W103L | HC |  | 0.85 |  |  |
| R95D S102V | HC | 0.01 | 11.92 |  |  |
| H94R R95D V100F S102V | HC | 0.64 | 3.44 |  |  |

TABLE 4-continued

| Substitution made (Kabat numbering) | LC or HC | Rel. Aggregation | Rel. Productivity | Rel. Thioflavin T binding | Rel. ANS binding |
|---|---|---|---|---|---|
| S100dF (D101-1)** P102V | HC | 0.15 | 8.61 | | |
| S100dF (D101-1)** P102Y | HC | 0.18 | 6.78 | | |
| S100dM (D101-1)** P102V | HC | 0.00 | 8.69 | | |
| S100dM (D101-1)** P102Y | HC | 0.13 | 6.40 | | |
| P102V W103L | HC | | 0.58 | | |
| P102Y, W103L | HC | | 0.44 | | |
| P102Y W103I | HC | | 0.39 | | |
| P102Y W103V | HC | | 0.50 | | |

VL CDR3 positions: Y91, P93 are also numbered by proximity to Kabat's C88 & R96 is also numbered by proximity to Kabat's F98 respectively

**VH CDR3 positions: Due to heterogeneity of CDR3 (heavy) Positions are also named according to proximity to D101 (invariable in Kabat)
All data shown relative to wild-type.

The invention claimed is:

1. A variant immunoglobulin comprising a light chain variable (VL) domain and a heavy chain variable (VH) domain;
   wherein the VL domain comprises a substitution at a position selected from the group consisting of 37, 45 and 46; and/or
   wherein the VH domain comprises a substitution at a position selected from the group consisting of 1, 17, 94, 95, 96, 100, 100d and 102,
   said variant immunoglobulin having both reduced aggregation propensity and increased productivity upon expression relative to an immunoglobulin lacking said substitutions.

2. A variant immunoglobulin according to claim 1, wherein the substitution is selected from the group consisting of substitution of the residue at position 37 in the VL domain sequence for Q or N; substitution of the residue at position 45 in the VL domain sequence for E, K, R, Q or V; substitution of the residue at position 46 in the VL domain sequence for L or Y; substitution of the residue at position 1 in the VH domain sequence for E, Q, D, A or V; substitution of the residue at position 17 in the VH domain sequence for R; substitution of the residue at position 94 in the VH domain sequence for R; substitution of the residue at position 95 in the VH domain sequence for D; substitution of the residue at position 96 in the VH domain sequence for A; or a substitution of the residue at position 100d in the VH domain sequence for F, G, L, P or M; and a substitution of the residue at position 102 in the VH domain sequence for A, F, H, I, L, V or Y.

3. A variant immunoglobulin according to claim 1, wherein the sequence of the variant immunoglobulin has up to 10 amino acid substitutions.

4. A variant immunoglobulin according to claim 1, wherein the sequence of the VH domain comprises substitutions at position 1 and position 102; substitutions at position 95 and position 102 or; substitutions at positions 100d and 102; and optionally further comprises substitutions at positions 94 and 100.

5. A variant immunoglobulin according to claim 4, wherein the residue at position 102 is substituted for A, F, H, I, L, V or Y and wherein the residue at position 1 is substituted for E, Q, D, A or V; or the residue at position 102 is substituted for A, F, H, I, L, V or Y and the residue at position 95 is substituted for E or D.

6. A variant immunoglobulin according to claim 1, wherein the sequence of the VL domain of the variant immunoglobulin comprises substitutions at position 37 and position 45.

7. A variant immunoglobulin according to claim 6, wherein the residue at position 37 is substituted for Q or N and wherein the residue at position 45 is substituted for R, K or E.

8. A variant immunoglobulin according to claim 1, wherein the residue at position 94 in the VH domain is substituted for R, K or T and the residue at position 95 in the VH domain is substituted for E or D and the residue at position 46 in the VL domain is substituted for K, R, H, F or S.

9. A variant immunoglobulin according to claim 1, wherein the variant immunoglobulin is humanised; expressed in a recombinant system; isolated and/or purified following expression or formulated with a pharmaceutically acceptable excipient.

* * * * *

SEQUENCE LISTING

<160> NUMBER OF SEQ ID NOS: 2

<210> SEQ ID NO 1
<211> LENGTH: 110
<212> TYPE: PRT
<213> ORGANISM: Homo sapiens

<400> SEQUENCE: 1

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Pro
                85                  90                  95

Glu Met Arg Val Phe Gly Gly Gly Thr Lys Leu Thr Val Leu
            100                 105                 110

<210> SEQ ID NO 2
<211> LENGTH: 121
<212> TYPE: PRT
<213> ORGANISM: Homo sapiens

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Thr Tyr Glu Gly Pro Thr Tyr Phe Ala Ser Asp Pro Trp Gly
            100                 105                 110

Gln Gly Thr Leu Val Thr Val Ser Ser
            115             120
```